(12) United States Patent
Malekmehr

(10) Patent No.: US 10,500,372 B2
(45) Date of Patent: Dec. 10, 2019

(54) GUIDEWIRE

(71) Applicant: Farshad Malekmehr, Los Angeles, CA (US)

(72) Inventor: Farshad Malekmehr, Los Angeles, CA (US)

( * ) Notice: Subject to any disclaimer, the term of this patent is extended or adjusted under 35 U.S.C. 154(b) by 0 days.

(21) Appl. No.: 16/045,441

(22) Filed: Jul. 25, 2018

(65) Prior Publication Data

US 2019/0038874 A1 Feb. 7, 2019

Related U.S. Application Data

(60) Provisional application No. 62/540,504, filed on Aug. 2, 2017.

(51) Int. Cl.
| | | |
|---|---|---|
| *A61B 5/00* | (2006.01) | |
| *A61M 25/01* | (2006.01) | |
| *A61B 17/00* | (2006.01) | |
| *A61M 25/09* | (2006.01) | |

(Continued)

(52) U.S. Cl.
CPC ... *A61M 25/0147* (2013.01); *A61B 17/00234* (2013.01); *A61M 25/09* (2013.01); *A61M 25/09016* (2013.01); *A61B 1/0055* (2013.01); *A61B 1/0057* (2013.01); *A61B 2017/00305* (2013.01); *A61B 2017/22047* (2013.01);
(Continued)

(58) Field of Classification Search
CPC .......... A61M 25/0108; A61M 25/0103; A61M 25/0144; A61M 25/0147; A61M 25/09016; A61M 25/09025; A61M 25/09033; A61M 25/09041; A61M 2025/015; A61M 2025/0915
See application file for complete search history.

(56) References Cited

U.S. PATENT DOCUMENTS 4,215,703 A * 8/1980 Willson .......... A61M 25/09033
600/585
5,297,443 A   3/1994 Wentz
(Continued)

FOREIGN PATENT DOCUMENTS

| WO | WO 2005/115524 A2 | 12/2005 |
| WO | WO 2014/089273 A1 | 6/2014 |
| WO | WO 2016/139589 A1 | 9/2016 |

OTHER PUBLICATIONS

Arora et al., "An Update on the Energy Sources and Catheter Technology for the Ablation of Atrial Fibrillation," Journal of Atrial Fibrillation, 2(5): 12-31, Mar.-May 2010.

(Continued)

*Primary Examiner* — Max F Hindenburg
(74) *Attorney, Agent, or Firm* — Lewis Roca Rothgerber Christie LLP

(57) ABSTRACT

A guidewire including a thin elongated structure and an outer shell around at least a portion of the thin elongated structure. The outer shell includes a first portion and a second portion. The first portion and the second portion of the outer shell are each coupled to the thin elongated structure. The first portion is spaced from the second portion by a gap. The guidewire is configured to move between a flexible state and a rigid state. The gap has a first distance when the guidewire is in the flexible state and the gap has a second distance greater than the first distance when the guidewire is in the rigid state.

11 Claims, 17 Drawing Sheets

(51) Int. Cl.
*A61B 17/22* (2006.01)
*A61B 1/005* (2006.01)
(52) U.S. Cl.
CPC ............ *A61M 2025/0915* (2013.01); *A61M 2025/09116* (2013.01)

(56) References Cited

U.S. PATENT DOCUMENTS

| | | | |
|---|---|---|---|
| 5,762,615 A * | 6/1998 | Weier | A61M 25/09 600/585 |
| 6,004,279 A | 12/1999 | Crowley et al. | |
| 6,183,420 B1 * | 2/2001 | Douk | A61M 25/09 600/434 |
| 6,338,725 B1 | 1/2002 | Hermann et al. | |
| 7,998,132 B2 * | 8/2011 | Gregorich | A61M 25/0045 604/525 |
| 2002/0004638 A1 * | 1/2002 | Soukup | A61M 25/09 600/585 |
| 2003/0105415 A1 | 6/2003 | Mirigian | |
| 2004/0186350 A1 | 9/2004 | Brenneman et al. | |
| 2005/0080400 A1 | 4/2005 | Corcoran et al. | |
| 2007/0149951 A1 | 6/2007 | Wu et al. | |
| 2007/0233105 A1 | 10/2007 | Nelson et al. | |
| 2009/0131831 A1 * | 5/2009 | Wright | A61M 25/09 600/585 |
| 2010/0145308 A1 | 6/2010 | Layman et al. | |
| 2011/0040282 A1 | 2/2011 | Uihlein | |
| 2012/0041421 A1 | 2/2012 | Nishigishi | |
| 2012/0191012 A1 * | 7/2012 | Chin | A61M 25/09 600/585 |
| 2014/0052107 A1 | 2/2014 | Voeller et al. | |
| 2014/0222128 A1 | 8/2014 | Dusbabek et al. | |
| 2014/0243592 A1 | 8/2014 | Kato et al. | |
| 2015/0216589 A1 | 8/2015 | Wittenberger et al. | |
| 2016/0375226 A1 | 12/2016 | Nabeshima et al. | |
| 2016/0375227 A1 | 12/2016 | Parodi et al. | |

OTHER PUBLICATIONS

International Search Report and Written Opinion for International Application No. PCT/US2018/043750, dated Jan. 15, 2019, 10 pages.

* cited by examiner

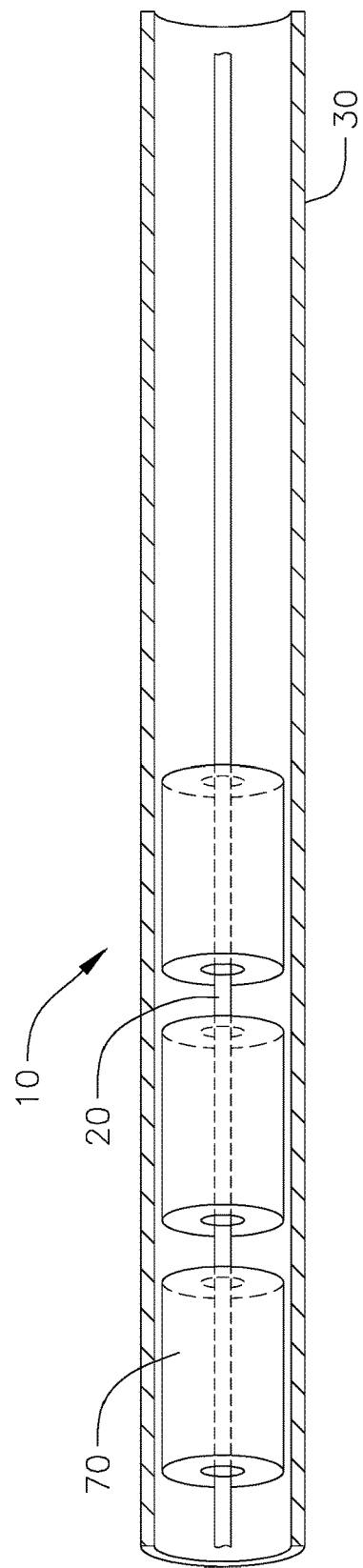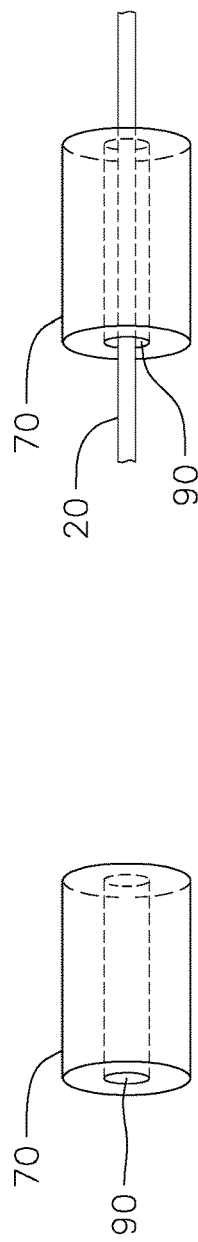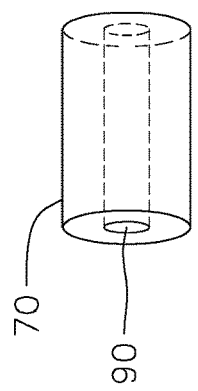

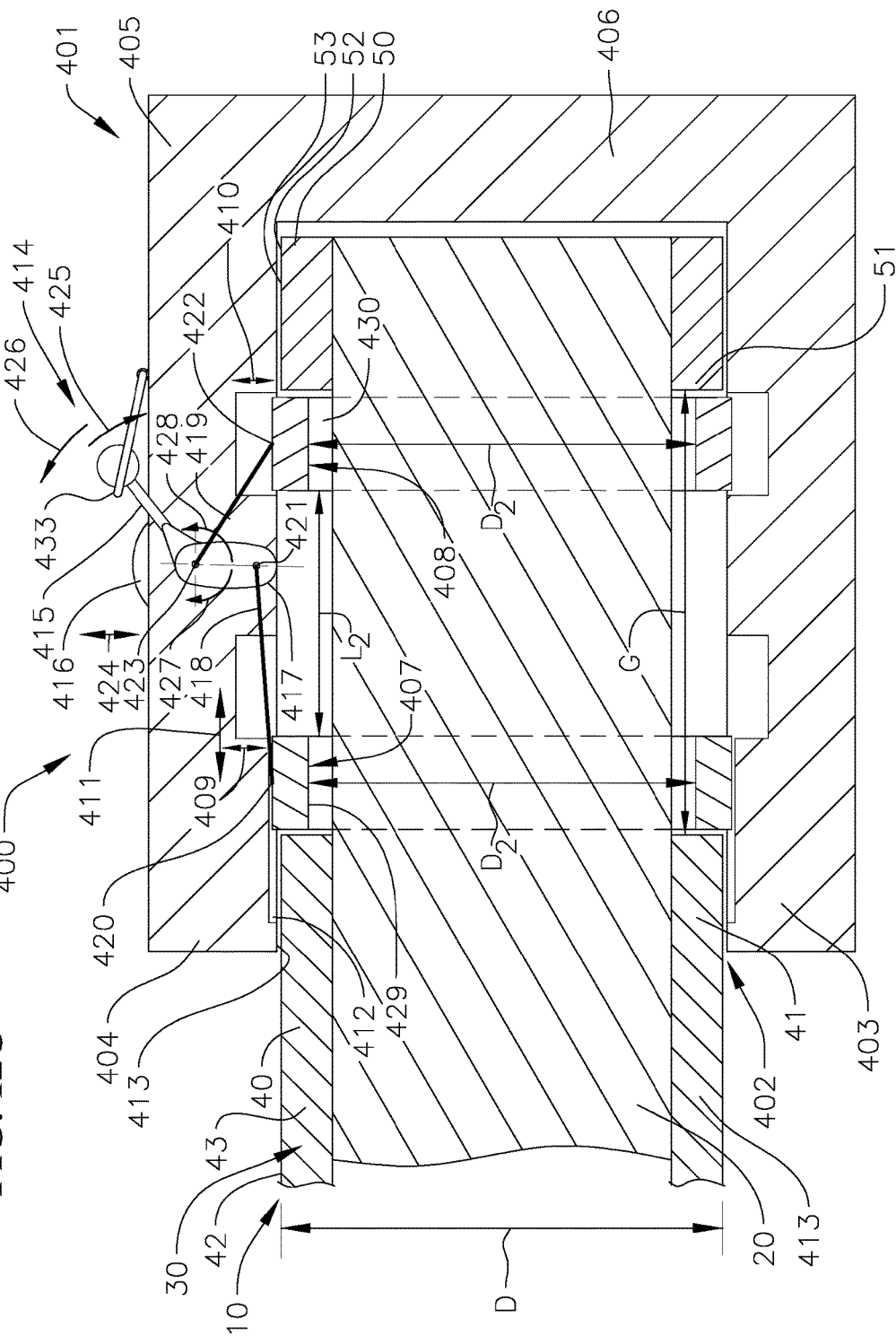

GUIDEWIRE

CROSS-REFERENCE TO RELATED APPLICATION(S)

This application claims priority to and the benefit of U.S. Provisional Application No. 62/540,504, filed Aug. 2, 2017, the entire contents of which are incorporated herein by reference.

FIELD

The present disclosure generally pertains to medical devices, and more particularly to medical guidewires such as intravascular guidewires and mechanisms for tensioning guidewires.

BACKGROUND

Guidewires are commonly used in conjunction with intravascular devices, for example intravascular catheters or other such devices, to facilitate navigation through the vasculature of a patient. The vasculature of a patient may be very tortuous. It is often desired that certain portions of a guidewire have lateral flexibility characteristics as well as pushability characteristics. It is also desirable that the guidewire be able to achieve a rigid state from a flexible state, to achieve a shape-locked configuration, and to revert to a flexible state from the rigid state.

SUMMARY

The present disclosure is directed to various embodiments of a guidewire. In one embodiment, the guidewire includes a thin elongated structure, and an outer shell around at least a portion of the thin elongated structure. The outer shell includes a first portion and a second portion each coupled to the thin elongated structure. The first portion is spaced from the second portion by a gap. The guidewire is configured to move between a flexible state and a rigid state. The gap has a first distance when the guidewire is in the flexible state and the gap has a second distance greater than the first distance when the guidewire is in the rigid state.

The first distance may be substantially zero.

The second distance may be at least approximately 1 cm.

The guidewire may include an outer stop coupled to the thin elongated structure.

The guidewire may also include an inner stop coupled to the first portion of the outer shell. The inner stop is configured to engage the outer stop when the guidewire is in the flexible state to maintain a minimum distance of the gap between the first portion and the second portion of the outer shell.

The outer stop may extend into the gap between the first portion and the second portion of the outer shell. The outer stop is configured to engage a proximal end of the first portion of the outer shell when the guidewire is in the flexible state to maintain a minimum distance of the gap between the first portion and the second portion of the outer shell.

The outer shell may include a spring.

The thin elongated structure may be a wire or a cable.

The present disclosure is also directed to various embodiments of a system. In one embodiment, the system includes a guidewire and a tensioning mechanism. The guidewire includes a thin elongated structure and an outer shell around a first portion of the thin elongated structure. A second portion of the thin elongated structure is exposed outside the thin elongated structure. The tensioning mechanism is configured to engage the second portion of the thin elongated structure to move the guidewire between a flexible state and a rigid state.

The tensioning mechanism may include a body portion defining a central opening having threads, and a flange portion extending from the body portion.

The thin elongated structure may include screw threads along at least a portion of the second portion, and the threads in the central opening of the tensioning mechanism may be configured to threadedly engage the screw threads of the thin elongated structure.

Rotating the tensioning mechanism in a first direction may move the guidewire from the flexible state to the rigid state, and rotating the tensioning mechanism in a second direction opposite the first direction may move the guidewire from the rigid state to the flexible state.

The system may also include an inwardly-extending flange at a proximal end of the outer shell, and an outer stop on the second portion of the thin elongated structure configured to engage the inwardly-extending flange when the guidewire is in the flexible state.

A length of an inner surface of the flange portion may be longer than a length of an outer surface of the outer stop.

An inner diameter of the flange portion may be larger than an inner diameter of central opening.

The tensioning mechanism may further include a taper extending between the inner surface of the flange portion and an inner surface of the central opening.

The present disclosure is also directed to various embodiments of a method of operating a guidewire comprising a thin elongated structure and an outer shell around at least a portion of the thin elongated structure. In one embodiment, the method includes moving the guidewire from a flexible state to a rigid state by pulling the thin elongated structure proximally.

The outer shell of the guidewire may include a first portion and a second portion each coupled to the thin elongated structure, and moving the guidewire from the flexible state to the rigid state may include increasing a length of a gap between the first portion of the outer shell and the second portion of the outer shell.

A second portion of the thin elongated structure may be exposed outside of the outer shell, and moving the guidewire from the flexible state to the rigid state may include threading a tensioning mechanism onto the second portion of the thin elongated structure.

The tensioning mechanism may include a body portion and a flange portion extending distally from the body portion, and the flange portion may engage a proximal end of the outer shell while moving the guidewire from the flexible state to the rigid state.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

FIG. 2 is a side view of a portion of a guidewire according to another embodiment of the present disclosure, the guidewire including a series of flexure members between a thin elongated structure and an outer shell;

FIG. 3 is a perspective view of the flexure member of the embodiment of the guidewire illustrated in FIG. 2;

FIG. 4 is a perspective view of the flexure member surrounding the thin elongated structure according to the embodiment of the guidewire illustrated in FIG. 2;

FIGS. 12A-12C are cross-sectional views of a tensioning mechanism configured to apply and release tension from a guidewire according to another embodiment of the present disclosure;

DETAILED DESCRIPTION

Figure 1A:
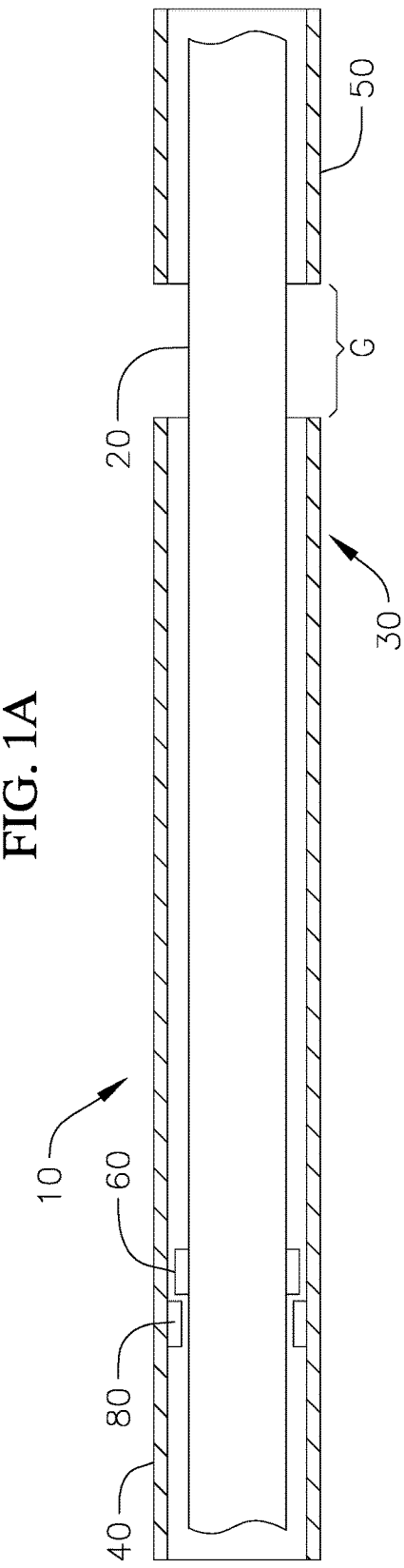
FIG. 1A is a side view of a portion of a guidewire according to one embodiment of the present disclosure.

The present disclosure is directed to various embodiments of a guidewire configured to move between a flexible state and a rigid state. The present disclosure is also directed to various embodiments of a tensioning mechanism configured to move the guidewire between the flexible and rigid states. Medical intervention inside a patient's blood vessel includes advancing a rigid device (e.g., a balloon catheter, a stent, an atherectomy device, or an intravascular ultrasound probe) over a guidewire. These rigid devices must navigate acute angles in the patient's blood vessel. As the rigid device is advanced through an acute angle, the rigid device can puncture the blood vessel and cause fatal bleeding. Conventionally, a flexible guidewire that is not prone to puncturing the blood vessel is first advanced into the patient's blood vessel and then the flexible guidewire is exchanged with a relatively stiffer guidewire over a soft catheter. The rigid device can then be passed over the stiffer guidewire to navigate acute angles without puncturing the blood vessel. However, each exchange of a relatively flexible guidewire for a relatively stiffer guidewire creates the risk of complications. For instance, each exchange increases the risk that the patient's blood vessel will be punctured by the guidewire. Additionally, exchanging the flexible guidewire for the relatively stiffer guidewire increases surgical time, and thus increases fluoroscopy exposure time for the patient and the attending medical staff. The present disclosure, which is directed to various embodiments of a guidewire configured to selectively move between a flexible state and a rigid state, is configured to reduce the number of exchanges that must occur during a medical intervention and thereby improve patient outcomes.

FIG. 1 shows a side view of a portion of a guidewire 10 in accordance with one example embodiment. The guidewire 10 includes a thin elongated structure 20 (e.g., a wire or a monofilament). An outer shell 30 including a first portion 40 and a second portion 50 surrounds the thin elongated structure 20. The outer shell 30 may have any suitable configuration, such as a spiral configuration (e.g., a coil spring), as is known in the art. A portion (e.g., a tip portion) of the first portion 40 of the outer shell 30 is coupled (e.g., welded) to a portion (e.g., a tip portion) of the thin elongated structure 20, as is well known in the art. Additionally, in one or more embodiments, the second portion 50 of the outer shell 30 is coupled (e.g., welded) to a portion of the thin elongated structure 20. In FIG. 1, a distal end 51 of the second portion 50 is spaced apart from a proximal end 41 of the first portion 40 (e.g., by a gap G). In one or more embodiments, the gap G exposes a portion of the thin elongated structure 20.

Additionally, in the embodiment shown, the guidewire 10 includes an outer stop (e.g., lock) 60 formed on the thin elongated structure 20. The outer stop 60 extends outward from the thin elongated structure 20 toward the first portion 40 of the outer shell 30. Additionally, in the illustrated embodiment, the guidewire 10 includes an inner stop (e.g., lock) 80 on the outer shell 30 configured to engage the outer stop 60. The inner stop 80 extends inward from the first portion 40 of the outer shell 30 toward the thin elongated structure 20. In the illustrated embodiment, the inner stop 80 is positioned between the outer stop 60 and the tip portions of the thin elongated structure 20 and the first portion 40 of the outer shell 30. The engagement between the outer stop 60 and the inner stop 80 is configured to keep the first portion 40 and second portion 50 of the outer shell 30 spaced apart by the gap G (e.g., the inner and outer stops 80, 60 are configured to prevent the gap G from completely closing).

In one or more embodiments, the guidewire 10 may be provided without the outer stop 60 (e.g., the guidewire 10 may be provided with only the inner stop 80 on the thin elongated structure 20). For instance, in the embodiment illustrated in FIG. 1B, the guidewire 10 is provided with only the inner stop 80 on the thin elongated structure 20, and the inner stop 80 extends into the gap G between the first portion 40 and the second portion 50 of the outer shell 30 (e.g., the inner stop 80 may be provided on a portion of the thin elongated structure 20 that is aligned with the gap G between the first portion 40 and the second portion 50 of the outer shell 30). Additionally, in the embodiment illustrated in FIG. 1B in which the inner stop 80 extends into the gap G between the first portion 40 and the second portion 50 of the outer shell 30, contact between the inner stop 80 and the proximal end 41 of the first portion 40 and/or the distal end 51 of the second portion 50 is configured to keep the first portion 40 and second portion 50 of the outer shell 30 spaced apart by the gap G (e.g., the contact between the inner stop 80 and the proximal end 41 of the first portion 40 of the outer shell 30 and/or the distal end 51 of the second portion 50 of the outer shell 30 is configured to prevent the gap G from completely closing). Additionally, in the illustrated embodiment, the proximal end 41 of the first portion 40 includes an inwardly extending flange 42 configured to engage the inner stop 80 on the thin elongated structure 20. In the illustrated embodiment, an outer surface 81 of the inner stop 80 is recessed below an outer surface 43 of the first portion 40 of the outer shell 30 (e.g., the outer surface 81 of the inner stop 80 is between the outer surface 43 and an inner surface 44 of the first portion 40 of the outer shell 30). In one or more embodiments, recessing the outer surface 81 of the inner stop 80 below the outer surface 43 of the first portion 40 is configured to enable a tensioning mechanism, described in detail below, to extend into the gap G and move the first and second portions 40, 50 of the outer shell 30 toward and away from each other.

The thin elongated structure 20 may be any suitable structure for use as a thin elongated structure, as will be understood by those of skill in the art and others. For example, the thin elongated structure 20 can be a wire or a cable. The thin elongated structure 20 can have a solid cross-section, but in some embodiments, can have a hollow cross-section. In yet other embodiments, the thin elongated structure 20 can include a combination of areas having solid cross-sections and hollow cross-sections.

The guidewire 10 is configured to move between a flexible configuration in which the guidewire 10 has lateral flexibility, and a rigid configuration (e.g., a shape-locked configuration) in which the guidewire 10 has relatively less lateral flexibility than when the guidewire 10 is in the flexible configuration. In one or more embodiments, when the guidewire 10 is in the flexible state, a distal end portion of the thin elongated structure 20 (e.g., a tip portion of the thin elongated structure 20) has a greater degree of flexibility than a remaining portion of the thin elongated structure 20. In one embodiment, the guidewire 10 may be moved from the flexible configuration to the rigid configuration by moving the first and second portions 40, 50 of the outer shell 30 away from each other such that the gap G between the first and second portions 40, 50 increases. In one or more embodiments, the gap G may be increased by advancing the first portion 40 of the outer shell 30 away from the second portion 50 of the outer shell 30 and/or retracting the second portion 50 away from the first portion 40 of the outer shell 30. As the first and second portions 40, 50 of the outer shell 30 are moved away from each other, the first portion 40, which is coupled to the thin elongated structure 20, pulls on the thin elongated structure 20 and thereby applies tension to the thin elongated structure 20. The tension applied to the thin elongated structure 20 by the first portion 40 of the outer shell 30 maintains the guidewire 10 in the rigid configuration. As the first and second portions 40, 50 of the outer shell 30 are moved toward each other such that the gap G between the first and second portions 40, 50 decreases, the thin elongated structure 20 relaxes (e.g., the tension supplied to the thin elongated structure 20 by the first portion 40 of the outer shell 30 is reduced), which returns the guidewire 10 to the flexible configuration. Accordingly, the guidewire 10 according to one embodiment of the present disclosure may be moved between the flexible configuration and the rigid configuration by moving the first portion 40 of the outer shell 30 away from and toward the second portion 50 of the outer shell 30 to increase and decrease, respectively, the gap G between the first and second portions 40, 50 of the outer shell 30. In one or more embodiments, the length of the gap G when the guidewire is in the flexible configuration may be zero or substantially zero. In one or more embodiments, the length of the gap G when the guidewire is in the rigid configuration may be at least approximately 0.5 cm. In one or more embodiments, the length of the gap G when the guidewire is in the rigid configuration may be at least approximately 1 cm.

Figure 1B:
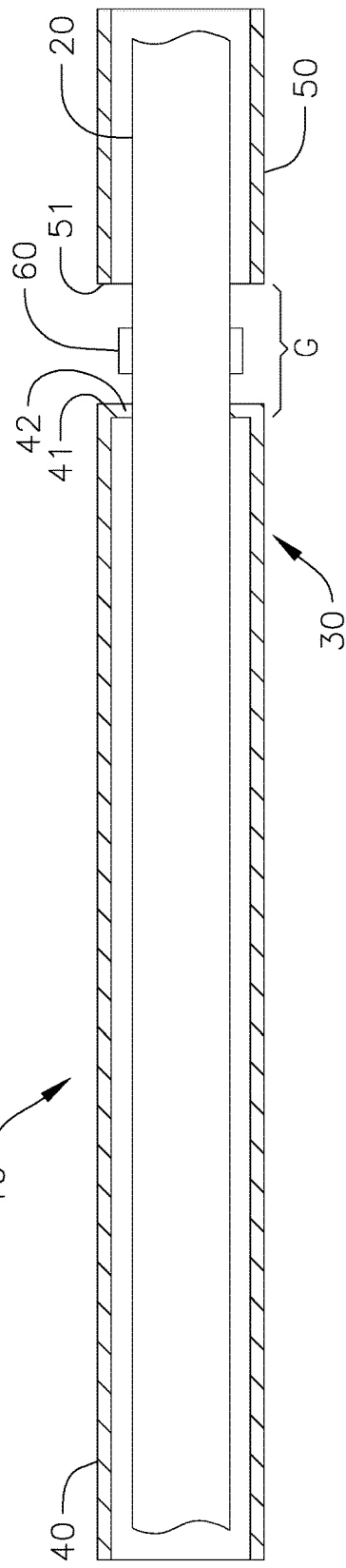
FIG. 1B is a side view of a portion of a guidewire according to another embodiment of the present disclosure.

In one or more embodiments in which the first portion 40, or at least a portion thereof, of the outer shell 30 has a spiral wound configuration (e.g., a coil spring), the first portion 40 is a resilient member configured to bias the guidewire 10 into the flexible configuration. For instance, in one or more embodiments, the resilient first portion 40 of the outer shell 30 is configured to bias the first portion 40 toward the second portion 50 such that the gap G between the first and second portions 40, 50 has a minimal length (e.g., the resiliency of the first portion 40 is configured to bias the first portion 40 toward the second portion 50 of the outer shell 30 such that the outer stop 80 contacts the inner stop 60, as illustrated in FIG. 1A, or the inner stop 60 contacts the proximal end 41 of the first portion 40, as illustrated in FIG. 1B).

Figure 5:
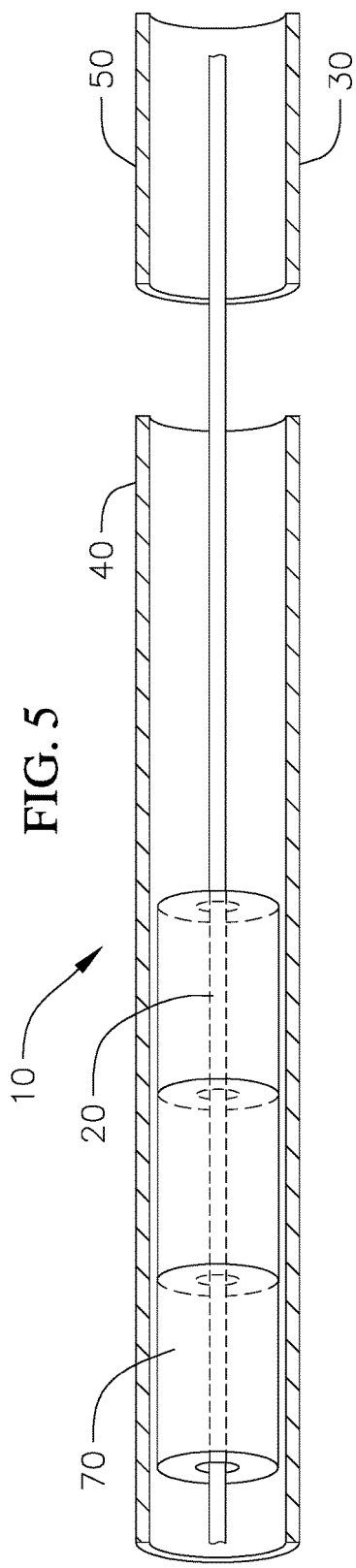
FIG. 5 is a side view of the embodiment of the guidewire illustrated in FIG. 2 with the series of flexure members engaging each other.

FIG. 2 illustrates another example embodiment of a guidewire 10 including a plurality of flexure members (or flexure sections) 70 interposed between the thin elongated structure 20 and the outer shell 30. In at least some embodiments, the flexure members 70 are cylinders. In at least some embodiments, each of the flexure members 70 is a separate and discrete structure spaced from any adjacent segment or segments (e.g., independent from any adjacent segment or segments). Each of the flexure members 70 is adapted and configured to be movable to contact with one or more segments that are adjacent thereto, as illustrated in FIG. 5. This allows lateral flexure (e.g., flexibility) of the guidewire 10. FIG. 3 shows an individual flexure member 70 containing an inner lumen 90 configured to surround the thin elongated structure 20. FIG. 4 illustrates the thin elongated structure 20 disposed through the inner lumen 90 of the flexure members 70.

In one or more embodiments, the number of flexure members 70 used in the guidewire 10 is dependent upon the desired length and/or flexibility characteristics of the guidewire 10. In one or more embodiments, the length of each flexure member can be varied dependent upon the desired length and/or flexibility characteristics of the guidewire 10. In one or more embodiments, all of the flexure members 70 within a guidewire 10 can be of generally uniform length, or can vary in length to achieve variable stiffness characteristics of a guidewire 10.

In one or more embodiments, each of the flexure members 70 is a hollow or generally tubular segment. Additionally, in one or more embodiments, each of the flexure members 70 includes engagement features to connect to another flexure member. Such engagement features can include any structure generally known to provide such a connection function. For example, each of the flexure members 70 can include side surfaces including engagement means (e.g., engagement structure), for example, crenations, teeth, serrations, bends, grooves, protrusions, notches, tongue and groove arrangements, or other arrangements, and the like, that are adapted and configured to mate with each other such that side surfaces of adjacent segments connect in a mechanical or frictional manner in relation to one another.

Figure 6:
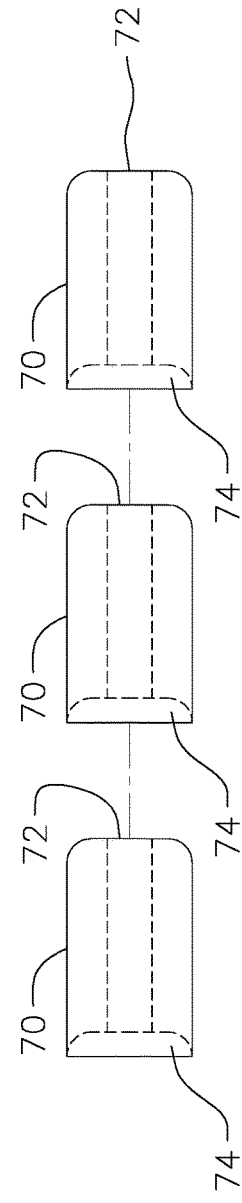
FIG. 6 is a side view of a series of flexure members according to another embodiment of the present disclosure.
Figure 7:
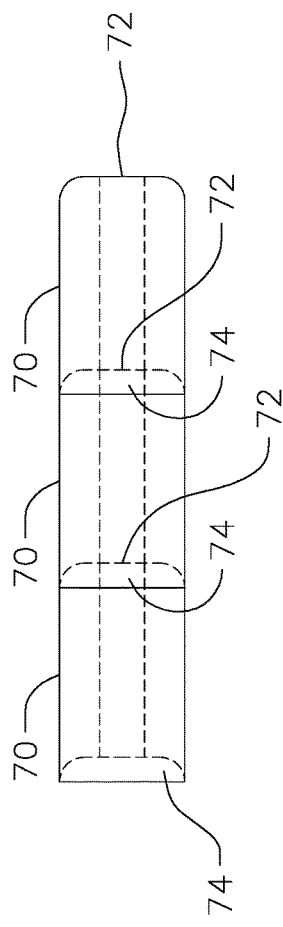
FIG. 7 is a side view of the embodiment of the flexure members illustrated in FIG. 6 showing the flexure members engaging each other.

In the embodiment illustrated in FIGS. 6-7, each of the flexure members 70 include opposing side surfaces 72 and 74. The side surfaces 72 include a male shape, and the side surfaces 74 include a female shape therein (e.g. convex and concave, etc.). The side surfaces 72 are adapted and configured to mate with the side surfaces 74 to provide a mechanical connection between adjacent segments 70. As seen in FIGS. 6-7, the side surfaces 72 and 74 of the multiple flexure members 70 are generally in line with each other along the length of the guidewire 10. FIG. 7 shows the flexure members 70 of FIG. 6, in a connected position. The connecting construction allows for movement into a rigid configuration.

In the illustrated embodiment, the outer shell 30 is disposed about at least a portion of the plurality of flexure members 70. In some embodiments, the outer shell 30 is also disposed about at least a portion of the thin elongated structure 20. The outer shell 30 is disposed over the plurality of flexure members 70, and can encapsulate the flexure members 70, yet allow the thin elongated structure 20 to flex and bend laterally. The outer shell 30 can be a spring or similar structure known to those skilled in the art.

When tension is applied to the thin elongated structure 20, the flexure members 70 mate with each other to provide a mechanical connection between adjacent segments. The guidewire 10 therefore goes from soft e.g., resting form to rigid (e.g., stiff) form and shape-locked in this configuration.

Figure 8A:
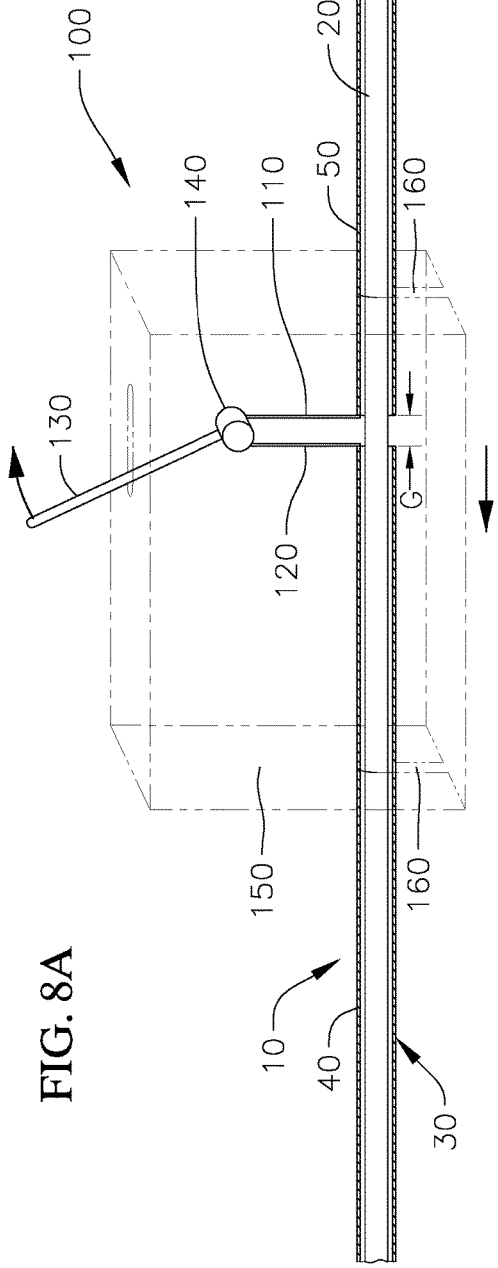
FIG. 8A is a side view of a tensioning mechanism configured to apply and release tension from a guidewire according to one embodiment of the present disclosure.
Figure 8B:
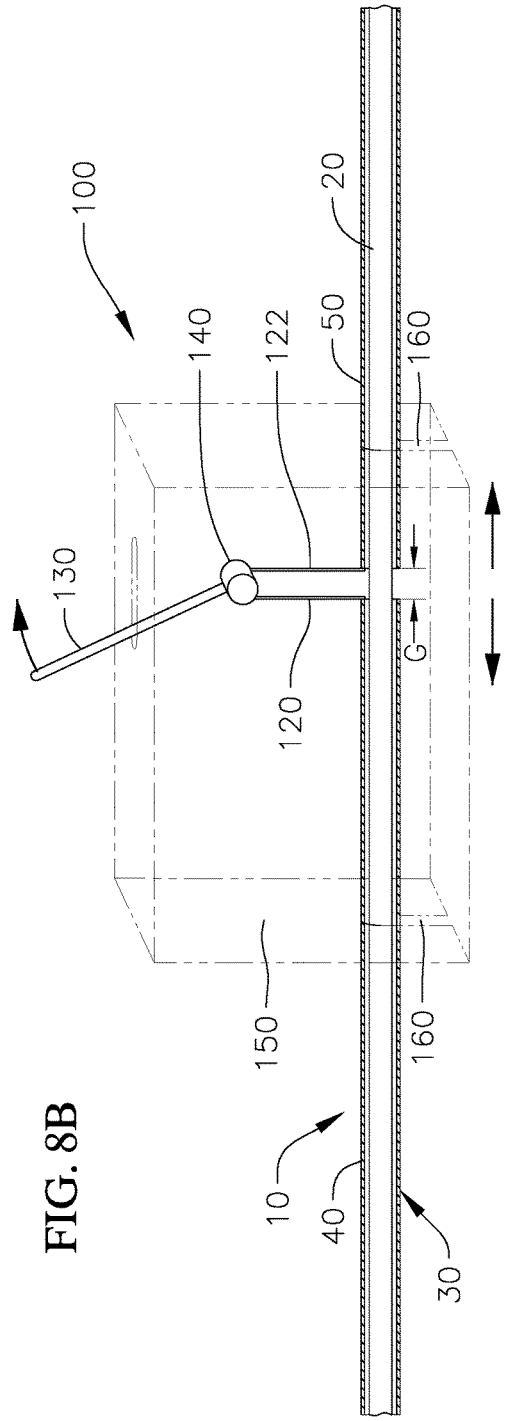
FIG. 8B is a side view of a tensioning mechanism configured to apply and release tension from a guidewire according to another embodiment of the present disclosure.

Now with reference to FIGS. 8A-8B, tensioning mechanisms are described wherein guidewire 10 is disposed at rest in the flexible (e.g., soft) configuration. In the embodiment illustrated in FIG. 8A, a tensioning mechanism 100 includes a fixed leg 110, a pivot leg 120, and a handle 130 all arranged around a central pivot 140, enclosed within a box 150. The box 150 has slits 160 formed thereon through which the guidewire 10 extends.

In order to transition the guidewire 10 from the flexible configuration to the rigid configuration, the fixed leg 110 is detachably engaged to a portion of the guidewire 10, such as at the second portion 50 of the outer shell 30. The fixed leg 110 is held stationary while the handle 130 is advanced. Pivot leg 120 rotates in the same direction as the handle 130 around the central pivot 140 and engages the guidewire 10, such as at the first portion 40 of the outer shell 30, and the pivot leg 120 applies force in the direction of the arrow shown in FIG. 8A, thereby increasing the gap G between the first and second portions 40 and 50 of the outer shell 30. Therefore, tensioning the guidewire 10 transitions the guidewire 10 to the rigid configuration and shape-locking in this configuration. To return the guidewire 10 to the flexible configuration, the handle 130 is released or returned, which causes the pivot leg 120 to cease applying force to the guidewire 10.

In FIG. 8B, the tensioning mechanism 100 has been modified, such that the fixed leg 110 is modified to become a pivot leg 122. As the handle 130 is advanced, the pivot legs 120 and 122 engage the guidewire 10 at the first portion 40 and the second portion 50 of the outer shell 30 and apply force in the direction of the arrows shown in FIG. 8B, thereby increasing the gap G between the first and second portions 40 and 50 of the outer shell 30. Therefore, tensioning the guidewire 10 transitions the guidewire 10 to the rigid configuration and shape-locking in this configuration. To return the guidewire 10 to the flexible configuration, the handle 130 is released or returned, which causes the pivot legs 120 and 122 to cease applying force to the guidewire 10.

Figure 8C:
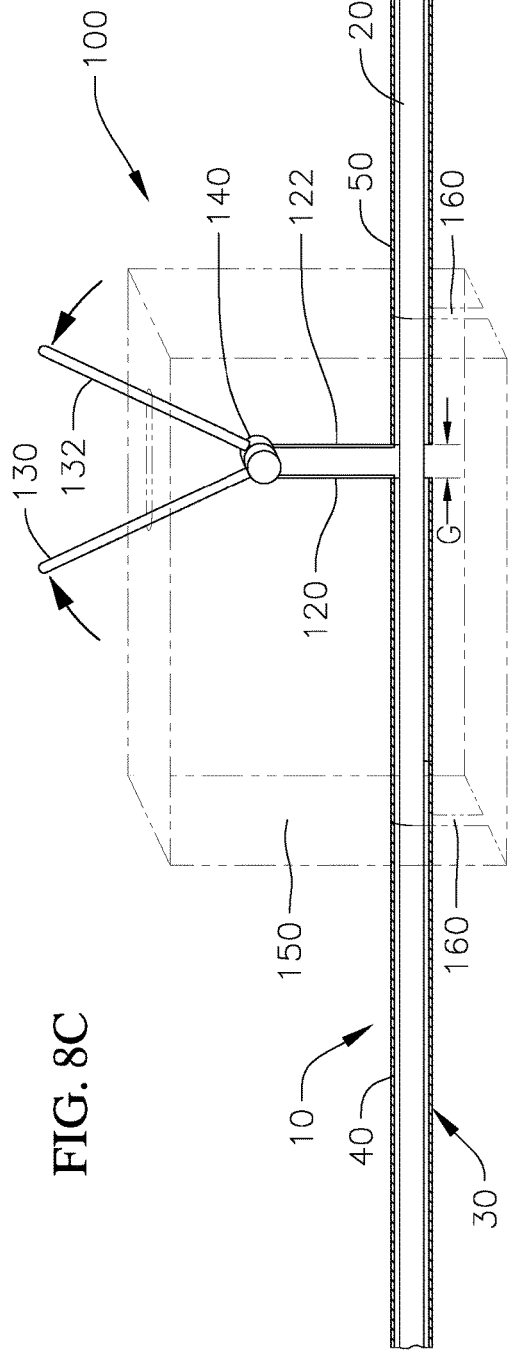
FIG. 8C is a side view of a tensioning mechanism according to another embodiment of the present disclosure configured to apply and release tension from a guidewire, where the tensioning mechanism is in an "open" configuration and the guidewire is in a flexible state.
Figure 8D:
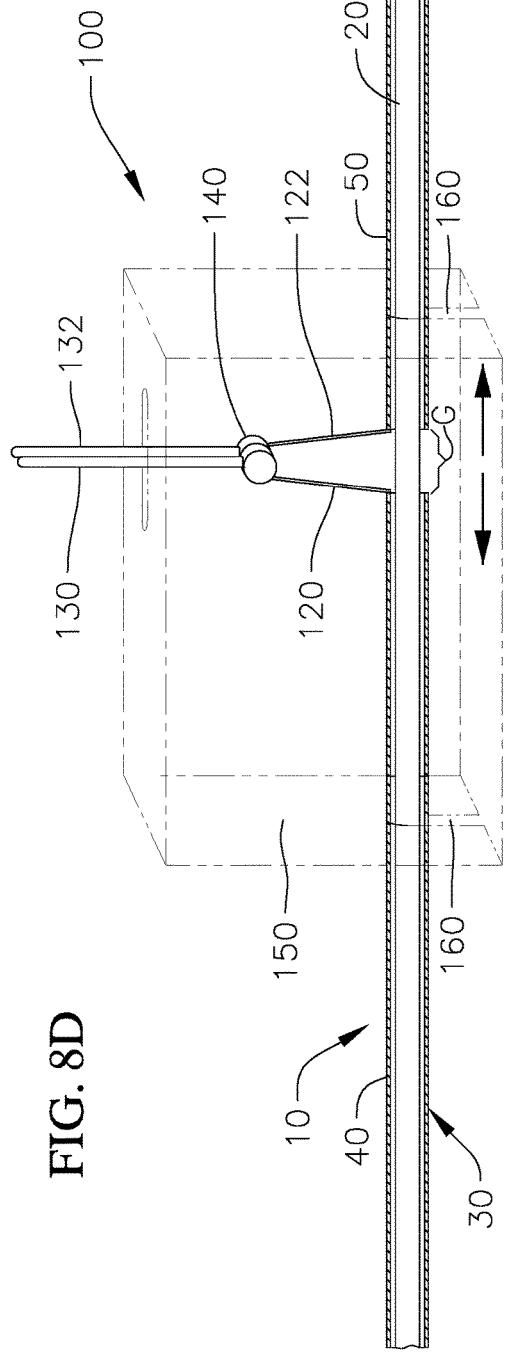
FIG. 8D is a side view of the embodiment of the tensioning mechanism illustrated in FIG. 8C, where the tensioning mechanism is in a "closed" configuration and the guidewire is in a rigid state.

In FIGS. 8C and 8D, the tensioning mechanism 100 has further been modified to add an additional handle 132 around the central pivot 140. In the configuration shown in FIG. 8C, the guidewire 10 is in a resting state. The handles 130 and 132 of the tensioning mechanism are in an "open" configuration. As the handles 130 and 132 are rotated towards each other, as shown in the arrows in FIG. 8D, the pivot legs 120 and 122 engage the guidewire 10 at first portion 40 and second portion 50, respectively, of the outer shell 30 and apply force in the direction of the arrows shown in FIG. 8D, thereby tensioning the guidewire 10 to the rigid configuration and shape-locking in this configuration. To return the guidewire 10 to the flexible configuration, the handles 130 and 132 are released or returned, which causes the pivot legs 120 and 122, respectively, to cease applying force to the guidewire 10.

Figure 9:
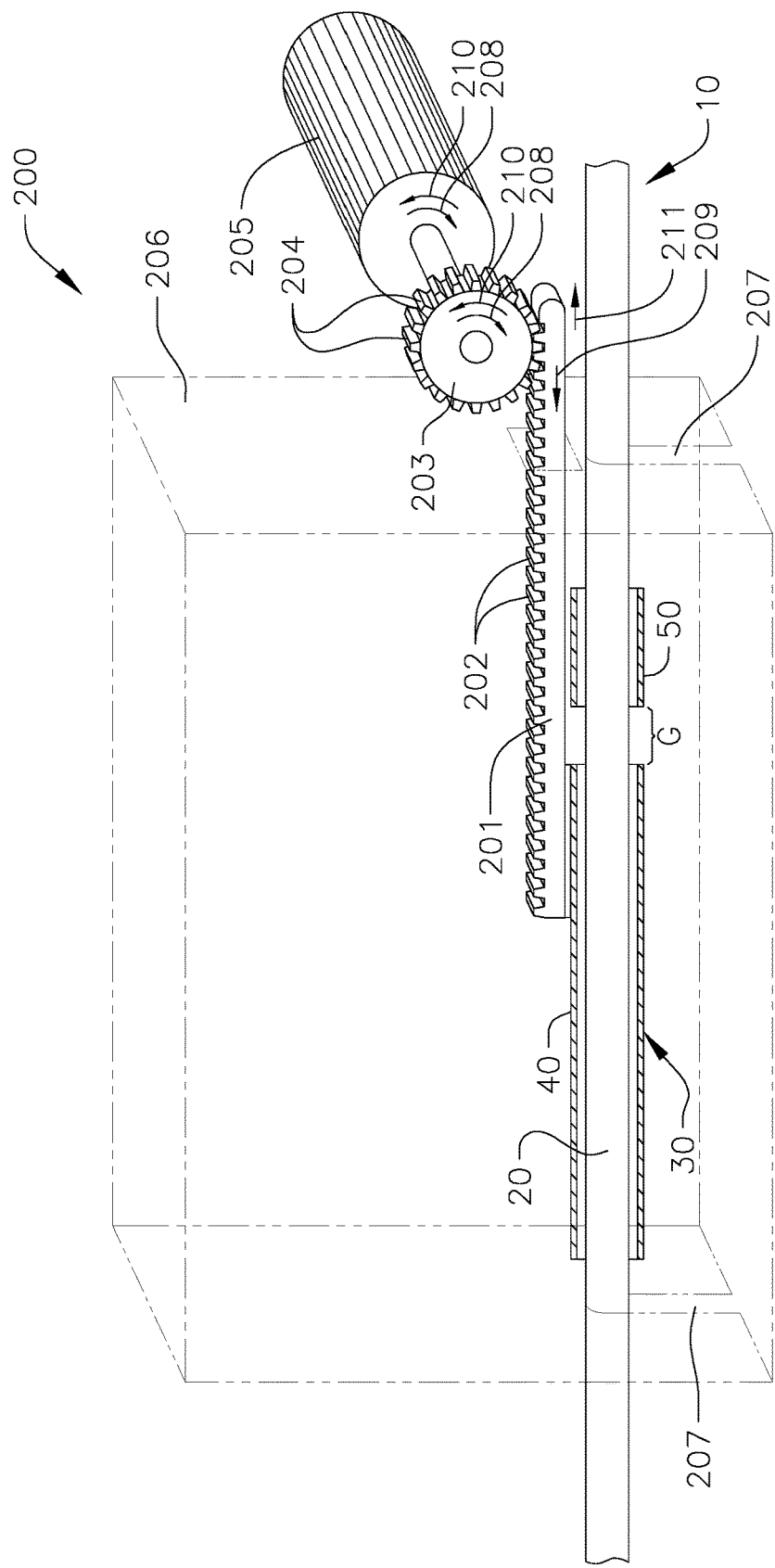
FIG. 9 is a side view of a tensioning mechanism configured to apply and release tension from a guidewire according to another embodiment of the present disclosure.

A tensioning mechanism 200 according to another embodiment is illustrated in FIG. 9. In the illustrated embodiment, the tensioning mechanism 200 includes a rack 201 having a series of teeth 202, a pinion 203 having a series of teeth 204 engaging the teeth 202 of the rack 201, and a motor 205 coupled to the pinion 203. In the illustrated embodiment, the rack 201 is coupled to the first portion 40 of the guidewire 10, although in one or more embodiments, the rack 201 may be coupled to the second portion 50 of the guidewire 10. Additionally, in the illustrated embodiment, the tensioning mechanism 200 includes a box 206 defining a slit 207 configured to accommodate a portion of the guidewire 10 extending through the slit 207.

Actuation of the motor 205 in a first direction (arrow 208) (e.g., clockwise) is configured to rotate the pinion 202 in the first direction (arrow 208), and rotation of the pinion 203 in the first direction (arrow 208) is configured to slide the rack 201 in a first direction (arrow 209), which causes the first portion 40 of the guidewire 10 to move away from the second portion 50 of the guidewire 10 and thereby moves the guidewire 10 into the rigid state (e.g., actuation of the motor 205 in the first direction (arrow 208) increases the gap G between the first and second portions 40, 50 of the outer shell 30 and thereby moves the guidewire 10 into the rigid state). Actuation of the motor 205 in a second direction (arrow 210) (e.g., counterclockwise) opposite the first direction is configured to rotate the pinion 202 in the second direction (arrow 210), and rotation of the pinion 203 in the second direction (arrow 210) is configured to slide the rack 201 in a second direction (arrow 211), which causes the first portion 40 of the guidewire 10 to move toward the second portion 50 of the guidewire 10 and thereby moves the guidewire 10 into the flexible state (e.g., actuation of the motor 205 in the second direction (arrow 210) decreases the gap G between the first and second portions 40, 50 of the outer shell 30 and thereby moves the guidewire 10 into the flexible state).

To transition the guidewire 10 from the flexible configuration to the rigid configuration, the guidewire 10 is inserted through the slit 207 in the box 206. In one or more embodiments, the box 206 is then connected to a portion of the guidewire 10, such as at the second portion 50 of the outer shell 30. The motor 205 is then actuated in the first direction 208 (e.g., clockwise), which moves the first portion 40 of the guidewire 10 away from the second portion 50 of the guidewire 10 and thereby moves the guidewire 10 into the rigid state in which the guidewire 10 is shape-locked. To return the guidewire 10 to the flexible configuration, the motor 205 is actuated in the second direction 210 (e.g., counterclockwise), which moves the first portion 40 of the guidewire 10 toward the second portion 50 of the guidewire 10 and thereby moves the guidewire 10 into the flexible state in which the guidewire 10 is laterally flexible.

Figure 10:
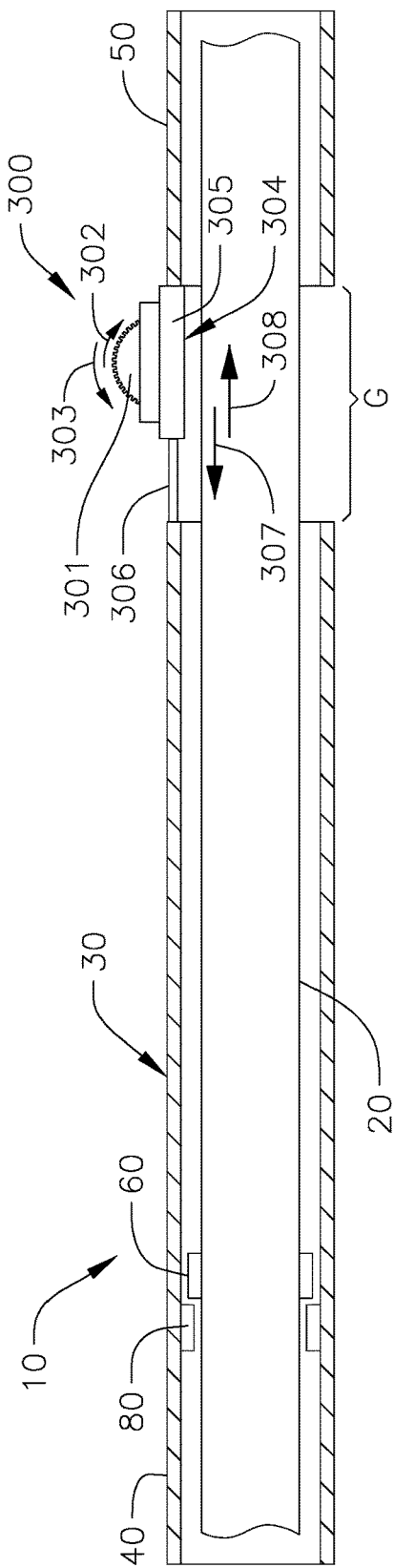
FIG. 10 is a side view of a tensioning mechanism configured to apply and release tension from a guidewire according to a further embodiment of the present disclosure.

FIG. 10 depicts a tensioning mechanism 300 according to another embodiment of the present disclosure. In the illustrated embodiment, the tensioning mechanism 300, or at least a portion thereof, is positioned in or proximate to the gap G between the first and second portions 40, 50 of the outer shell 30. In the illustrated embodiment, the tensioning mechanism 300 includes a thumbwheel 301. Actuation of the thumbwheel 301 (e.g., rotation of the thumbwheel 301 with the user's thumb) in a first direction (arrow 302) is configured to move the first and second portions 40, 50 further apart from each other (e.g., rotation of the thumbwheel 301 in the first direction 302 is configured to increase the length of the gap G between the first and second portions 40, 50 of the outer shell 30), and thereby move the guidewire 10 into the rigid state. Actuation (e.g., rotation) of the thumbwheel 301 in a second direction (arrow 303) opposite to the first direction is configured to move the first and second portions 40, 50 closer to each other (e.g., rotation of the thumbwheel 301 in the second direction 303 is configured to decrease the length of the gap G between the first and second portions 40, 50 of the outer shell 30), and thereby return the guidewire 10 to the flexible state. The thumbwheel 301 may be operably to any suitable mechanism or mechanism for increasing and decreasing the length of the gap G between the first and second portions 40, 50 of the outer shell 30. For instance, in one or more embodiments, the thumbwheel 301 may be operably coupled to a linear actuator 304 (e.g., a telescoping linear screw) that is coupled at opposite ends to the first and second portions 40, 50 of the outer shell 30. In the illustrated embodiment, the linear actuator 304 is a telescoping linear screw including a first segment 305 and a second segment 306 at least partially telescopically housed in the first segment 305. The first segment 305 of the telescoping linear screw is coupled to the second portion 50 of the outer shell 30, and the second segment 306 of the telescoping linear screw is coupled to the first portion 40 of the outer shell 30. In one or more embodiments, actuation of the thumbwheel 301 in the first direction (arrow 302) is configured to lengthen (arrow 307) the telescoping linear screw 304 (e.g., actuation of the thumbwheel 301 in the first direction (arrow 302) is configured to extend (arrow 307) the second segment 306 further out of the first segment 305 of the telescoping linear screw) and thereby increase the length of the gap G between the first and second portions 40, 50. Additionally, in one or more embodiments, actuation of the thumbwheel 301 in the second direction (arrow 303) is configured to shorten (arrow 308) the telescoping linear screw 304 (e.g., actuation of the thumbwheel 301 in the second direction (arrow 303) is configured to retract (arrow 308) the second segment 306 further into the first segment 305 of the telescoping linear screw) and thereby decrease the length of the gap G between the first and second portions 40, 50 of the outer shell 30. In this manner, the thumbwheel 301 and the telescoping linear screw 304 are configured to move the guidewire 10 between the flexible state and the rigid state. In one or more embodiments, the thumbwheel 301 may be operably coupled to a motor configured to increase and decrease the length of the gap G between the first and second portions 40, 50 of the outer shell 30 to move the guidewire 10 between the flexible and rigid states.

Figure 11A:
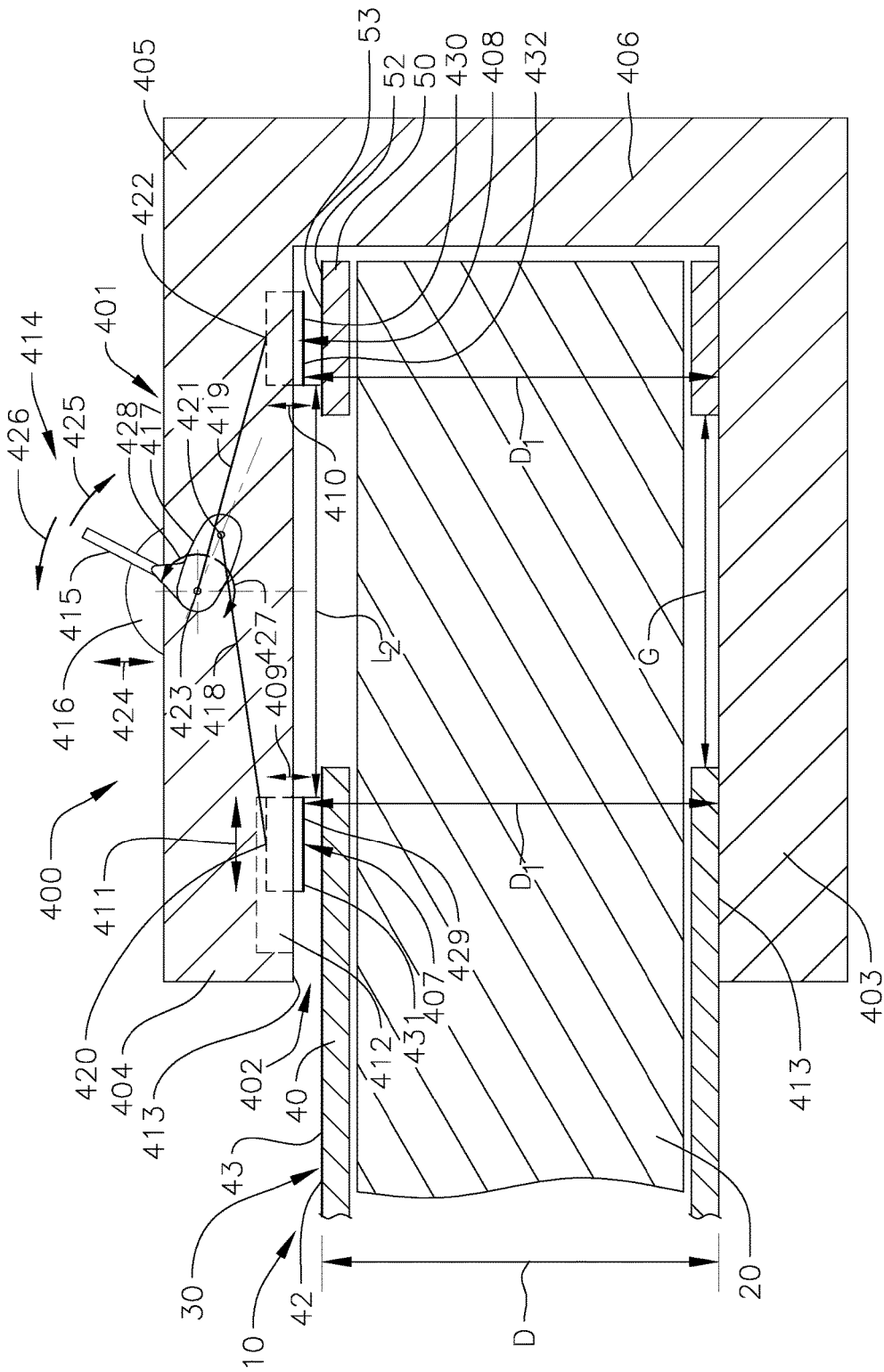
FIGS. 11A-11C are cross-sectional views of a tensioning mechanism configured to apply and release tension from a guidewire according to a further embodiment of the present disclosure.
Figure 11B:
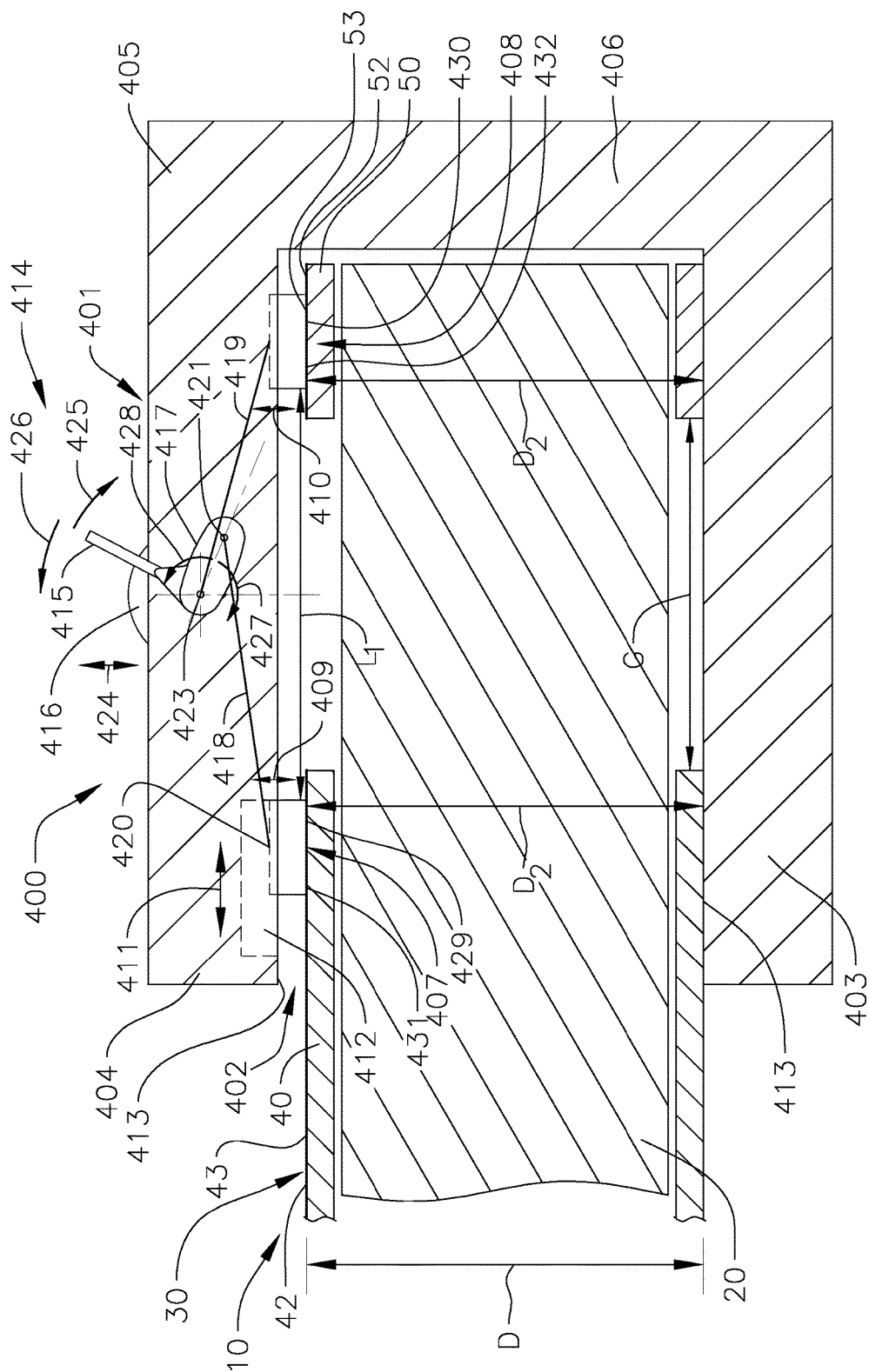
Figure 11C:
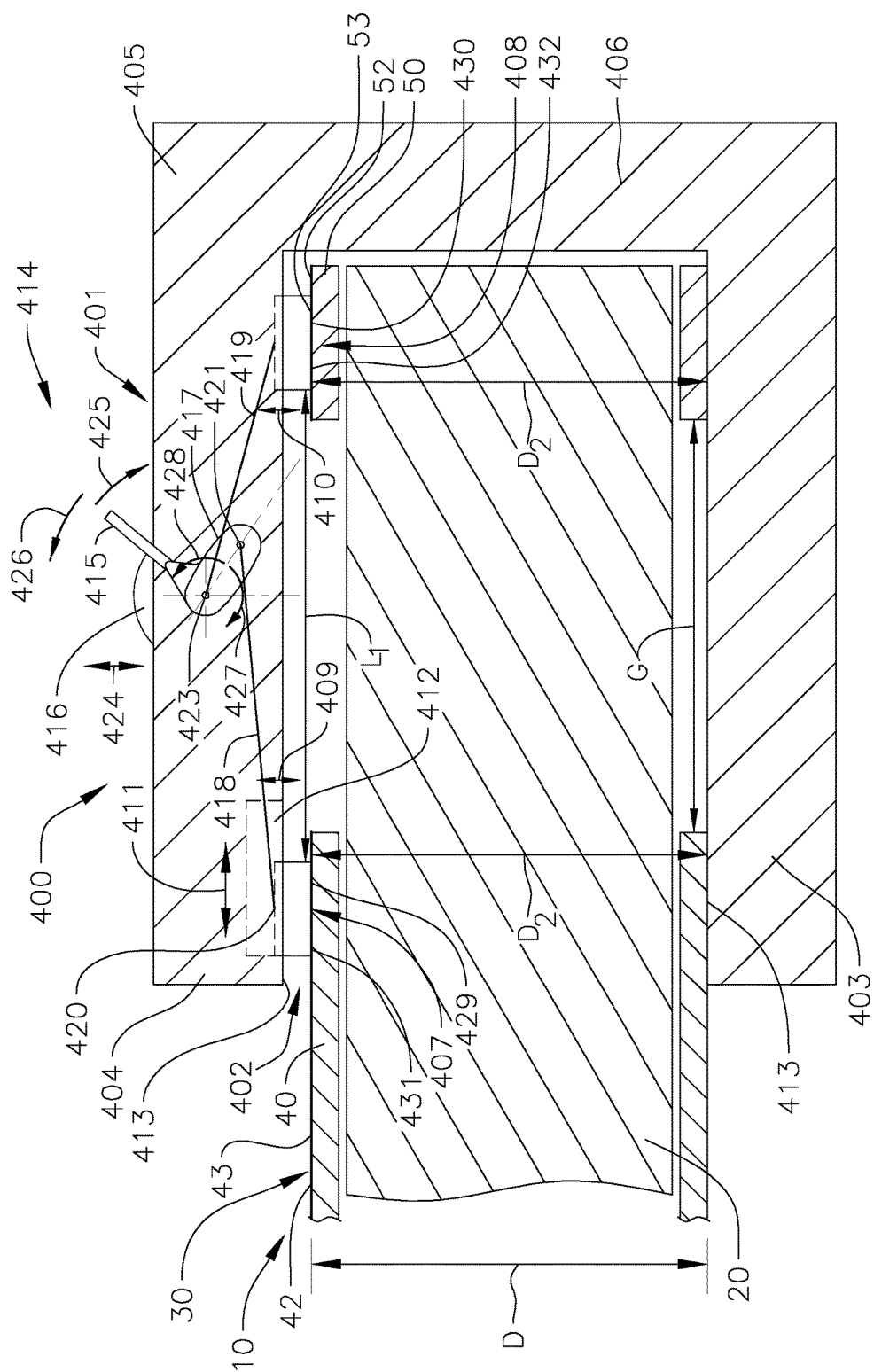

FIGS. 11A-11C depict a tensioning mechanism 400 according to another embodiment of the present disclosure. In the illustrated embodiment, the tensioning mechanism 400 includes a body 401 defining a central opening 402 (e.g., a blind bore hole or a through hole). In the illustrated embodiment, the body 401 of the tensioning mechanism 400 is tubular (e.g., a hollow cylindrical member), although in one or more embodiments, the body 401 may have any other suitable shape. In the illustrated embodiment, the body 401 includes a sidewall 403 (e.g., a cylindrical sidewall) having a distal end 404 and a proximal end 405 opposite the distal end 404, and an end wall 406 at the proximal end 405 of the sidewall 403. Together, the sidewall 403 and the end wall 406 define the central opening 402. Additionally, in the illustrated embodiment, the central opening 402 is a blind bore terminating at the end wall 406. In one or more embodiments, the body 401 may be provided without the end wall 406 and the central opening 402 may be a through hole that extends completely through the body 401. Additionally, in the illustrated embodiment, the distal end 404 of the body 401 is open such that the guidewire 10 may be inserted into the central opening 402.

In the embodiment illustrated in FIGS. 11A-11C, the tensioning mechanism 400 also includes a first pad 407 and a second pad 408 movably coupled to the sidewall 403 of the body 401. In the illustrated embodiment, the first and second pads 407, 408 are spaced apart from each other along the lengthwise direction of the sidewall 403 such that the tensioning mechanism 400 includes a relatively distal pad 407 and a relatively proximal pad 408. In the illustrated embodiment, the first pad 407 is proximate to the distal end 404 of the sidewall 403 and the second pad 408 is proximate to the proximal end 405 of the sidewall 403. In the illustrated embodiment, the first pad 407 and the second pad 408 are both annular members (e.g., a snap ring or a retaining ring).

In one or more embodiments, the first pad 407 and the second pad 408 are each configured to move (arrows 409, 410, respectively) between a retracted position (shown in FIG. 11A) and an extended position (shown in FIGS. 11B-11C). In the illustrated embodiment in which the sidewall 403 is cylindrical, the first and second pads 407, 408 are configured to move radially (arrows 409, 410) inward and outward between the retracted and extended positions. In the extended position, the first and second pads 407, 408 extend a greater distance into the central opening 402 than when the first and second pads 407, 408 are in the retracted position. In one or more embodiments, the first and second pads 407, 408 may not extend into or may substantially not extend into the central opening 402 when the first and second pads 407, 408 are in the retracted position.

Additionally, in the illustrated embodiment, the first pad 407 is slidably coupled (arrow 411) to the sidewall 403 of the body 401 such that first pad 407 is configured to slide along the sidewall 403 toward and away (arrow 411) from the second pad 408. In the illustrated embodiment, the first pad 407 is configured to slide (arrow 411) between a first position in which the first pad 407 is spaced apart from the second pad 408 by a first length $L_1$ along a lengthwise direction of the sidewall 403 of the body 401 to a second position in which the first pad 407 is spaced apart from the second pad 408 by a second length $L_2$ along the lengthwise direction of the sidewall 403 of the body 401 that is greater than the first length $L_1$. In the illustrated embodiment, the first pad 407 is at least partially slidably accommodated in a track 412 in an inner surface 413 of the sidewall 403.

Although in the illustrated embodiment the tensioning mechanism 400 includes two pads 407, 408, in one or more embodiments, the tensioning mechanism 400 may include any other suitable number of pads. For instance, in one or more embodiments, the first pad 407 may include a series of first pad segments arranged around the inner circumference of the sidewall 403, and the second pad 408 may include a series of second pad segments arranged around the inner circumference of the sidewall 403. In one or more embodiments, the first pad 407 may include at least a pair of opposing first pad segments (e.g., two pairs of opposing first pad segments), and the second pad 408 may include at least a pair of opposing second pad segments (e.g., two pairs of opposing second pad segments).

Additionally, in the illustrated embodiment, the tensioning mechanism 400 includes an actuator 414 coupled to the body 401 and operably coupled to the first and second pads 407, 408. The actuator 414 is configured to move (arrows 409, 410) the first and second pads 407, 408 between the retracted and extended positions (e.g., the actuator 414 is configured to move the pads 407, 408 radially inward and outward). In the illustrated embodiment, the actuator 414 is also configured to slide (arrow 411) the first pad 407 toward and away from the second pad 408. As described in more detail below, moving the pads into the extended positions is configured to connect the first pad to the first portion of the guidewire and the second pad to the second portion of the guidewire, and moving the first pad toward and away from the second pad is configured to decrease and increase, respectively, the length of the gap G between the first and second portions 40, 50 of the outer shell 30 and thereby move the guidewire 10 between the flexible state and the rigid state.

In the illustrated embodiment, the actuator 414 includes a switch 415 and a button 416. Additionally, in the illustrated embodiment, the switch 415 is coupled to a cam 417, the first pad 407 is coupled to the cam 417 by a first linkage 418 (e.g., a first lever), and the second pad 408 is coupled to the cam 417 by a second linkage 419 (e.g., a second lever). In one embodiment, a first end 420 of the first linkage 418 is fixedly coupled to the first pad 407 and a second end 421 of the first linkage 418 opposite the first end 420 is rotatably coupled to the cam 417 (e.g., by a hinge pin). Additionally, in the illustrated embodiment, a first end 422 of the second linkage 419 is fixedly coupled to the second pad 408 and a second end 423 of the second linkage 419 opposite the first end 422 is rotatably coupled to the cam 417 (e.g., by a hinge pin).

Depressing (arrow 424) the button 416 relative to the sidewall 403 is configured to move (arrows 409, 410) the first and second pads 407, 408 from the retracted position to the extended position. In the illustrated embodiment, depressing (arrow 424) the button 416 is configured to move the cam 417 toward the inner surface 413 of the sidewall 403, and the movement of the cam 417 is configured to move the first and second linkages 418, 419, which moves the first and second pads 407, 408, respectively, into the extended positions. In one or more embodiments, the button 416 may include a spring-loaded lock mechanism configured to retain the button 416 in the depressed position until the button 416 is pressed again, which returns the button 416 to the initial position.

Rotation (arrows 425, 426) of the switch 415 is configured to slide (arrow 411) the first pad 407 along the sidewall 403 toward and away from the second pad 408 (e.g., rotation of the switch 415 in the first direction 425 is configured to separate the first and second pads 407, 408 further from each other, and rotation of the switch 415 in the second direction 426 and draw the first and second pads 407, 408 closer to each other). In the illustrated embodiment, rotation of the switch 415 in the first direction (arrow 425) rotates the cam 417 in a first direction (arrow 427), which causes the first end 420 of the first linkage 418, and the first pad 407 coupled thereto, to move toward the distal end 404 of the sidewall 403 and thereby increase the distance between the first and second pads 407, 408 along the sidewall 403. In the illustrated embodiment, rotation of the switch 415 in the second direction (arrow 426) rotates the cam 417 in a second direction (arrow 428), which causes the first end 420 of the first linkage 418, and the first pad 407 coupled thereto, to move toward the proximal end 405 of the sidewall 403 and thereby decrease the distance between the first and second pads 407, 408 along the sidewall 403.

In one or more embodiments, the tensioning mechanism 400 may include a lock 433 configured to lock the switch 415 into the desired position. In the illustrated embodiment, the lock 433 is rotatably coupled to the body 401 of the tensioning mechanism 400 and the lock 433 is configured to rotate between a stowed position (shown in FIGS. 12A-12B) in which the lock 433 is not engaging the switch 415 and an engaged position (shown in FIG. 12C) in which the lock 433 engages the switch 415 to prevent rotation (arrows 425, 426) of the switch 415. In one or more embodiments, the lock 433 may have any other suitable configuration. Accordingly, in one or more embodiments, the switch 415 may be rotated (arrow 425 or 426) to achieve the desired amount of tension in, and the rigidity of, the guidewire 10 and then the lock 433 may be moved into the engaged position (e.g., activated) to lock the switch 415 into the set position to maintain the desired tension and rigidity in the guidewire 10. The lock 433 may be moved into the stowed position (e.g., released) to adjust the tension in, and the rigidity of, the guidewire 10 (e.g., the lock 433 may be released to allow the switch 415 to be rotated (arrow 426) to return the guidewire 10 to the flexible configuration).

Although in the illustrated embodiment the tensioning mechanism 400 includes a single actuator 414 configured to both move (arrow 409, 410) the first and second pads 407, 408 into the extended position and slide (arrow 411) the first pad 407 along the sidewall 403 toward and away from the second pad 408, in one or more embodiments, the tensioning mechanism 400 may include separate actuators for moving the first and second pads 407, 408 into the extended position and sliding the first pad 407 along the sidewall 403 toward and away from the second pad 408 (e.g., the tensioning mechanism 400 may include a first actuator configured to move the first and second pads 407, 408 into the extended position and a second actuator configured to slide the first pad 407 along the sidewall 403 toward and away from the second pad 408).

In operation, a proximal end of the guidewire 10 may first be inserted into the central opening 402 in the tensioning mechanism 400. In one or more embodiments in which the central opening 402 is a blind bore, the guidewire 10 may be inserted into the central opening 402 until the proximal most end of the guidewire 10 contacts the end wall 406. Providing the end wall 406 on the tensioning mechanism 400 is configured to ensure proper alignment between the guidewire 10 and the tensioning mechanism 400. In the illustrated embodiment, the depth of the central opening 402 is selected such that the first pad 407 at least partially overlaps (e.g., completely overlaps) the first portion 40 of the outer shell 30 of the guidewire 10 and the second pad 408 at least partially overlaps (e.g., completely overlaps) the second portion 50 of the outer shell 30 of the guidewire 10 when the guidewire 10 is fully inserted into the central opening 402 in the tensioning mechanism 400 such that the proximal most end of the guidewire 10 contacts the end wall 406. In one or more embodiments in which the central opening 402 in the tensioning mechanism 400 is a through hole, the guidewire 10 may be inserted into the central opening 402 until the first pad 407 overlaps with the first portion 40 of the outer shell 30 and the second pad 408 overlaps with the second portion 50 of the outer shell 30. In one or more embodiments, the outer shell 30 of the guidewire 10 may include visual indicia (e.g., one or more markings) to aid in alignment between the guidewire 10 and the tensioning mechanism 400.

Once the guidewire 10 has been inserted into the central opening 402 of the tensioning mechanism 400, the tensioning mechanism 400 may be secured to the guidewire 10. In the illustrated embodiment, the tensioning mechanism 400 may be secured to the guidewire 10 by depressing (arrow 424) the button 416 of the actuator 414. As described above, depressing the button 416 of the actuator 414 moves the first and second pads 407, 408 into the extended positions. In the illustrated embodiment, when the first and second pads 407, 408 are in the extended positions, an inner surface 429 of the first pad 407 engages an outer surface 42 of the first portion 40 of the outer shell 30 and an inner surface 430 of the second pad 408 engages an outer surface 52 of the second portion 50 of the outer shell 30. The engagement between the inner surfaces 429, 430 of the first and second pads 407, 408 and the outer surfaces 42, 52 of the first and second portions 40, 50 of the outer shell 30 are configured to secure the tensioning mechanism 400 to the guidewire 10.

In one or more embodiments, the inner surfaces 429, 430 of the first and second pads 407, 408 may include one or more friction-inducing features 431, 432, respectively, such as, for instance, projections (e.g., a knurled surface) and/or depressions (e.g., grooves, striations, and/or dimples). Additionally, in one or more embodiments, portions of the first and second portions 40, 50 of the outer shell 30 that are configured to be engaged by the first and second pads 407, 408 may be solid (e.g., the portions of the first and second portions 40, 50 of the outer shell 30 that are configured to be engaged by the first and second pads 407, 408 may be solid and remaining portions of first portion 40 and the second portion 50 may be a coil spring). Additionally, the outer surfaces 42, 52 of the first and second portions 40, 50 of the outer shell 30 may include one or more friction-inducing features 43, 53, respectively, such as, for instance, projections (e.g., a knurled surface) and/or depressions (e.g., grooves, striations, and/or dimples).

Figure 12A:
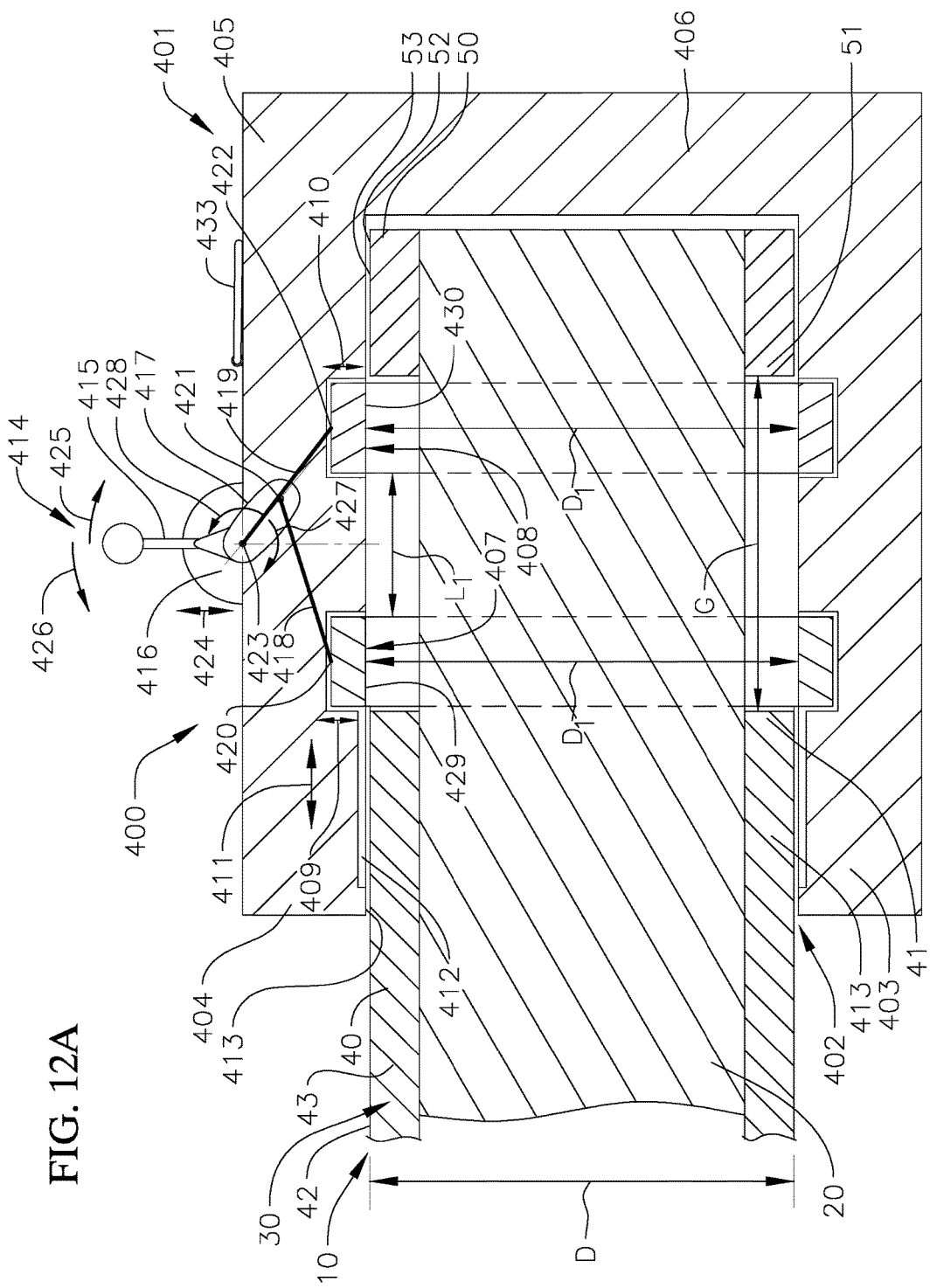

In the illustrated embodiment, when the first and second pads 407, 408 are in the retracted positions shown in FIG. 12A, the inner surface 429 of the first pad 407 and the inner surface 430 of the second pad 408 each have a diameter $D_1$ that is greater than an outer diameter D of the outer shell 30 of the guidewire 10, which permits the guidewire 10 to be inserted into the central opening 402 of the tensioning mechanism 400. When the first and second pads 407, 408 are in the extended positions, the inner surface 429 of the first pad 407 and the inner surface 430 of the second pad 408 each have a diameter $D_2$ less than the diameter $D_1$. In one or more embodiments, the diameter $D_2$ of the inner surfaces 429, 430 of the first and second pads 407, 408 when the first and second pads 407, 408 are in the extended position is equal to or less than the outer diameter D of the outer shell 30. Accordingly, in one or more embodiments, when the first and second pads 407, 408 are in the extended positions, the first and second pads 407, 408 engage the first and second portions 40, 50, respectively, of the outer shell 30 with an interference fit or a friction fit.

Once the tensioning mechanism 400 is secured to the guidewire 10 (e.g., by the first and second pads 407, 408 engaging the first and second portions 40, 50, respectively, of the outer shell 30), the tensioning mechanism 400 may be operated to move the guidewire 10 between the flexible state and the rigid (e.g., shape-locked) state. In the illustrated embodiment, the switch 415 may be rotated in the first direction (arrow 425) to move the guidewire 10 into the rigid state. As described above, rotating the switch 415 in the first direction (arrow 425) is configured to cause the first pad 407 to slide (arrow 411) along the sidewall 403 away from the second pad 408. This sliding movement of the first pad 407 moves the first portion 40 of the outer shell 30 away from the second portion 50 of the outer shell 30, due to the engagement between the inner surface 429 of the first pad 407 and the outer surface 42 of the first portion 40 of the outer shell 30, thereby increasing the length of the gap G between the first and second portions 40, 50 and moving the guidewire 10 into the rigid state. To return the guidewire 10 to the flexible state, the switch 415 may be rotated in the second direction (arrow 426) opposite the first direction. In the illustrated embodiment, rotating the switch 415 in the second direction (arrow 426) causes the first pad 407 to slide (arrow 411) along the sidewall 403 toward the second pad 408, and this sliding movement of the first pad 407 moves the first portion 40 of the outer shell 30 toward the second portion 50 of the outer shell 30 and reduces the length of the gap G between the first and second portions 40, 50 thereby moving the guidewire 10 into the flexible state.

Figure 12B:
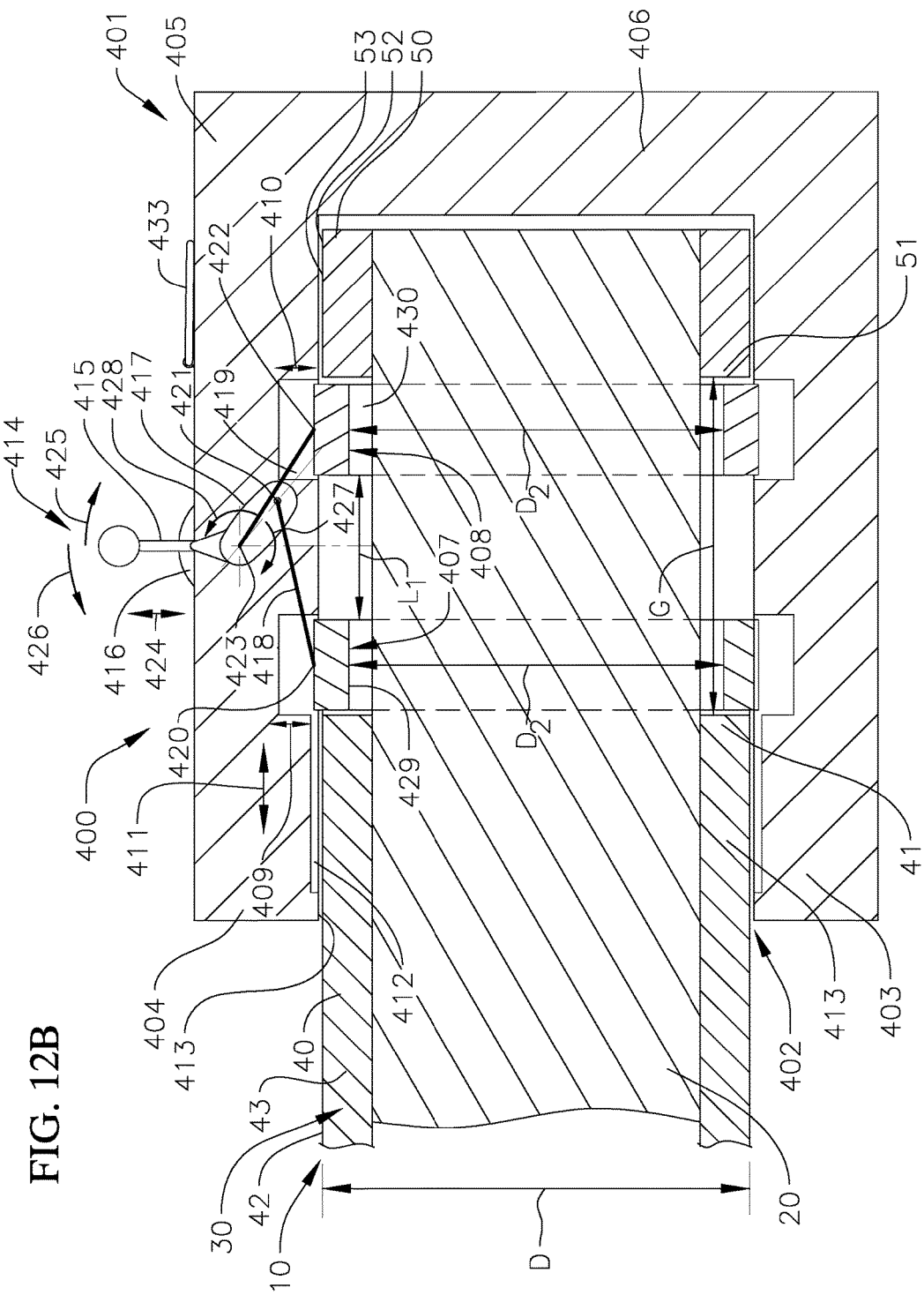

In one or more embodiments, the first and second pads 407, 408 may be configured to extend into the gap G between the first and second portions 40, 50 of the outer shell 30 to move the guidewire 10 between the flexible and rigid states, as illustrated, for instance, in the embodiment shown in FIGS. 12A-12C. To operate the tensioning mechanism 400 illustrated in FIGS. 12A-12C, a proximal end of the guidewire 10 may first be inserted into the central opening 402 in the tensioning mechanism 400 when the first and second pads 407, 408 are both in the retracted position. In the illustrated embodiment, when the first and second pads 407, 408 are in the retracted positions shown in FIG. 12A, the inner surface 429 of the first pad 407 and the inner surface 430 of the second pad 408 each have a diameter $D_1$ that is greater than an outer diameter D of the outer shell 30 of the guidewire 10, which permits the guidewire 10 to be inserted into the central opening 402 of the tensioning mechanism 400. In one or more embodiments in which the central opening 402 is a blind bore, the guidewire 10 may be inserted into the central opening 402 until the proximal most end of the guidewire 10 contacts the end wall 406. Providing the end wall 406 on the tensioning mechanism 400 is configured to ensure proper alignment between the guidewire 10 and the tensioning mechanism 400. In the illustrated embodiment, the depth of the central opening 402 is selected such that the first pad 407 and the second pad 408 are both aligned with the gap G between the first and second portions 40, 50 of the outer shell 30 when the guidewire 10 is fully inserted into the central opening 402 in the tensioning mechanism 400 such that the proximal most end of the guidewire 10 contacts the end wall 406. In one or more embodiments in which the central opening 402 in the tensioning mechanism 400 is a through hole, the guidewire 10 may be inserted into the central opening 402 until the first pad 407 and the second pad 408 are both aligned with the gap G between the first and second portions 40, 50 of the outer shell 30. In one or more embodiments, the outer shell 30 of the guidewire 10 may include visual indicia (e.g., one or more markings) to aid in alignment between the guidewire 10 and the tensioning mechanism 400.

Once the guidewire 10 has been inserted into the central opening 402 of the tensioning mechanism 400, the button 416 of the actuator 414 may be depressed (arrow 424) to move (arrows 409, 410) the first and second pads 407, 408 into the extended positions. In the embodiment illustrated in FIG. 12B, when the first and second pads 407, 408 are in the extended positions, the diameters $D_2$ of the inner surfaces 429, 430 of the first and second pads 407, 408, respectively, are less than the outer diameter D of the outer shell 30, and the inner surfaces 429, 430 of the first and second pads 407, 408, respectively, extend into the gap G between the first and second portions 40, 50 of the outer shell 30. Accordingly, in the illustrated embodiment, when the first and second pads 407, 408 are in the extended positions, at least a portion of the first pad 407 overlaps in a radial direction with the first portion 40 of the outer shell 30 and at least a portion of the second pad 408 overlaps in a radial direction with the second portion 50 of the outer shell 30. In one or more embodiments, the first and second pads 407, 408 may partially extend into the gap G between the first and second portions 40, 50 of the outer shell 30 when the button 416 is depressed (arrow 424) and the first and second pads 407, 408 are in the extended positions illustrated in FIG. 12B. In one or more embodiments, the first and second pads 407, 408 may completely or substantially completely extend into the gap G between the first and second portions 40, 50 of the outer shell 30 when the button 416 is depressed (arrow 424) and the first and second pads 407, 408 are in the extended positions.

Once the button 416 has been depressed (arrow 424) to move (arrows 409, 410) the first and second pads 407, 408 into the extended positions extending into the gap G between the first and second portions 40, 50 of the outer shell 30, the tensioning mechanism 400 may be operated to move the guidewire 10 between the flexible state and the rigid (e.g., shape-locked) state. In the embodiment illustrated in FIG. 12C, the switch 415 may be rotated in the first direction (arrow 425) to move the guidewire 10 into the rigid state. As described above, rotating the switch 415 in the first direction (arrow 425) is configured to cause the first pad 407 to slide (arrow 411) along the sidewall 403 away from the second pad 408. This sliding movement of the first pad 407 moves the first portion 40 of the outer shell 30 away from the second portion 50 of the outer shell 30 due to the engagement between the first pad 407 and the proximal end 41 of the first portion 40 of the outer shell 30, thereby increasing the length of the gap G between the first and second portions 40, 50 and moving the guidewire 10 into the rigid state. Additionally, in the illustrated embodiment, the second pad 408 engages the distal end 51 of the second portion 50 and thereby holds the second portion 50 in place as the first pad 407 engages the proximal end 41 of the first portion 40 and moves the first portion 40 away from the second portion 50 of the outer shell 30. To return the guidewire 10 to the flexible state, the switch 415 may be rotated in the second direction (arrow 426) opposite the first direction. In the illustrated embodiment, rotating the switch 415 in the second direction (arrow 426) causes the first pad 407 to slide (arrow 411) along the sidewall 403 toward the second pad 408, and this sliding movement of the first pad 407 permits the first portion 40 of the outer shell 30 to move toward the second portion 50 of the outer shell 30, thereby reducing the length of the gap G between the first and second portions 40, 50 and moving the guidewire 10 into the flexible state. In one or more embodiments, the first portion 40 may move toward the second portion 50 of the outer shell 30 due to the resiliency of the first portion 40 (e.g., the resiliency of the coil spring of the first portion 40 of the outer shell 30) as the first pad 407 slides (arrow 411) toward the second pad 408.

Figure 13A:
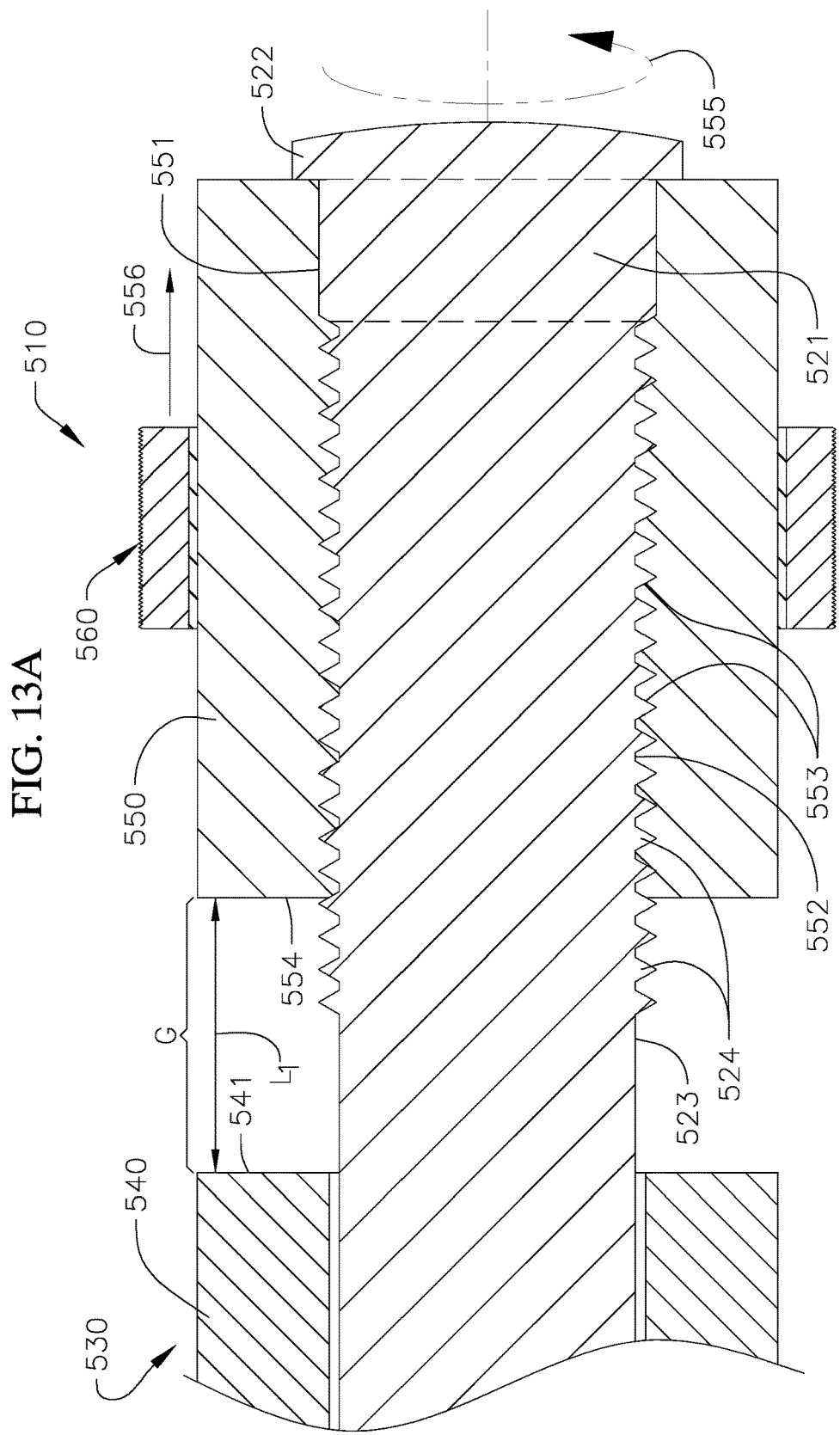
FIGS. 13A-13B are cross-sectional views of a guidewire according to another embodiment of the present disclosure.
Figure 13B:
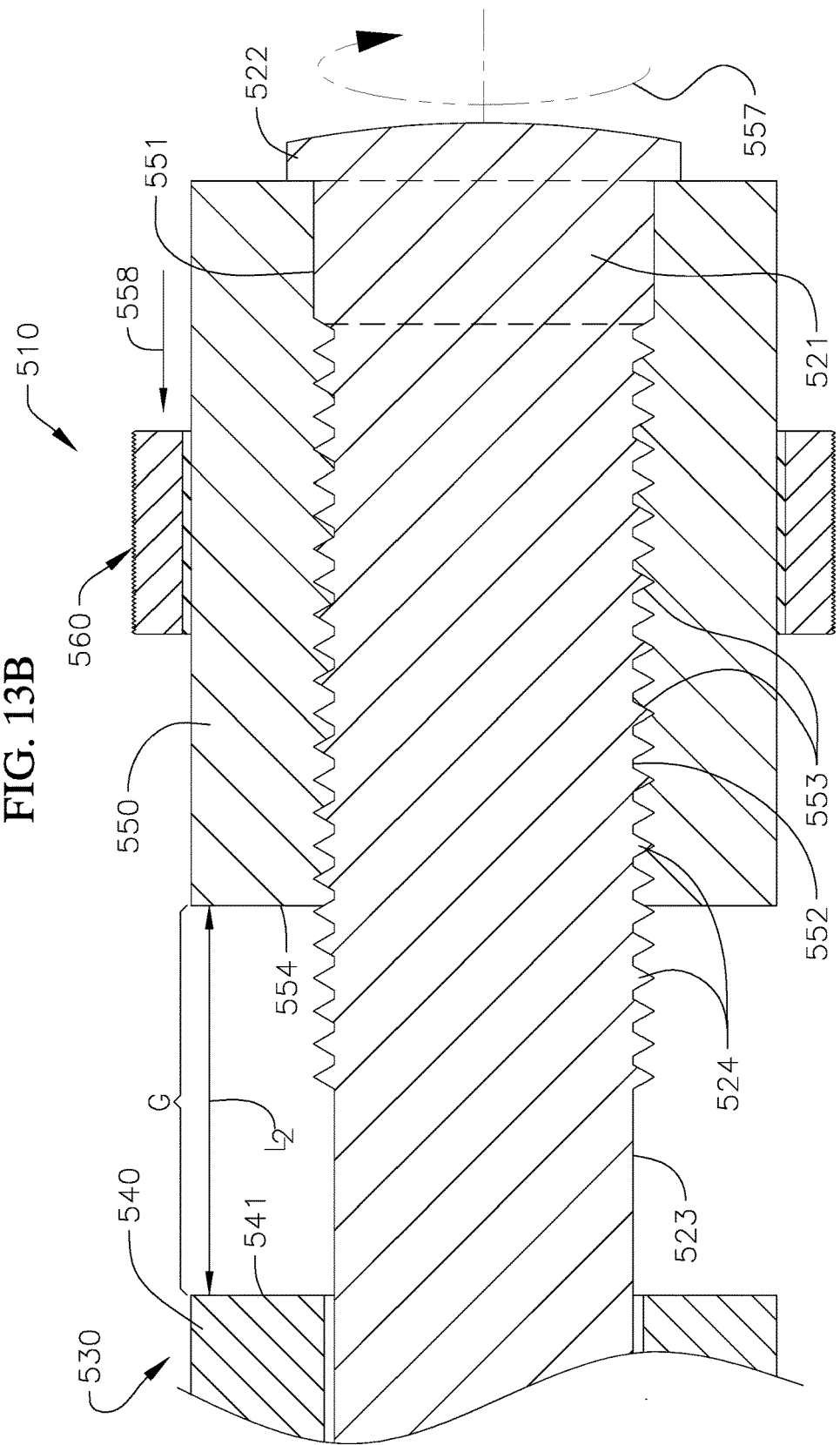

With reference now to FIGS. 13A-13B, a guidewire 510 according to another embodiment of the present disclosure includes a thin elongated structure 520 (e.g., a wire or a monofilament) and an outer shell 530 surrounding the thin elongated structure 520. In the illustrated embodiment, the outer shell 530 includes a first portion 540 and a second portion 550. The first portion 540 and the second portion 550 of the outer shell 530 may have any suitable configuration. For instance, in one or more embodiments, at least a portion of the first portion 540 and at least a portion of the second portion 550 may each have a spiral wound configuration (e.g., a coil spring). In one or more embodiments, at least a portion of the first portion 540 and at least a portion of the second portion 550 may each be solid. In one or more embodiments, the first portion 540 and/or the second portion 550 include both a solid portion and a spiral wound (e.g., coil spring) portion. In the illustrated embodiment, a portion (e.g., a tip portion) of the first portion 540 of the outer shell 530 is coupled (e.g., welded) to a portion (e.g., a tip portion) of the thin elongated structure 520. Additionally, in the illustrated embodiment, a portion of the second portion 550 of the outer shell 530 is coupled to a portion (e.g., a proximal portion) of the thin elongated structure 520. In the illustrated embodiment, a proximal end portion 521 of the thin elongated structure 520 extends through an opening 551 in the second portion 550 of the outer shell 530, and the proximal end portion 521 of the thin elongated structure 520 includes an enlarged portion 522 (e.g., a flange) configured to prevent the thin elongated structure 520 from withdrawing from the opening 551 and disengaging the second portion 550 of the outer shell 530.

In the illustrated embodiment, an inner surface 552 of the second portion 550 of the outer shell 530 includes threads 553, and an outer surface 523 of the thin elongated structure 520 includes screw threads 524 configured to threadedly engage the threads 553 in the second portion 550 of the outer shell 530. In one or more embodiments, the screw threads 524 may be provided only along a portion of the thin elongated structure 520 that is configured to be engaged by the threads 553 in the second portion 550 of the outer shell 530.

The guidewire 510 is configured to move between a flexible state (flexible configuration), illustrated in FIG. 12A, in which the guidewire 510 has lateral flexibility, and a rigid state (rigid configuration) (e.g., a shape-locked configuration), illustrated in FIG. 12B, in which the guidewire 510 has relatively less lateral flexibility. In the flexible state illustrated in FIG. 12A, a proximal end 541 of the first portion 540 of the outer shell 530 is spaced apart from a distal end 554 of the second portion 550 of the outer shell 530 by a gap G having a length $l_1$. In the rigid state illustrated in FIG. 12B, the gap G between the proximal end 541 of the first portion 540 of the outer shell 530 and the distal end 554 of the second portion 550 of the outer shell 530 has a length $l_2$ greater than the length $l_1$ of the gap G when the guidewire 510 is in the flexible state. In one or more embodiments, the length $l_1$ of the gap G when the guidewire 510 is in the flexible configuration may be zero or substantially zero. In one or more embodiments, the length $l_2$ of the gap G when the guidewire 510 is in the rigid configuration may be at least approximately 0.5 cm. In one or more embodiments, the length $l_2$ of the gap G when the guidewire 510 is in the rigid configuration may be at least approximately 1 cm.

In one embodiment, the guidewire 510 may be moved from the flexible configuration to the rigid configuration by rotating, relative to the thin elongated structure 520, the second portion 550 of the outer shell 530 in a first direction (arrow 555) (e.g., counterclockwise). In the illustrated embodiment, the passage of the proximal end 521 of the thin elongated structure 520 through the opening 551 in the second portion 550 is configured to prevent the rotation of the second portion 550 from twisting the thin elongated structure 520 (e.g., rotation of the second portion 550 of the outer shell 530 is not imparted to the thin elongated structure 520). As the second portion 550 of the outer shell 530 is rotated (arrow 555) relative to the thin elongated structure 520, the engagement between the screw threads 524 on the thin elongated structure 520 and the threads 553 of the second portion 550 causes the second portion 550 to move (arrow 556) away from the first portion 540 of the outer shell 530 such that the gap G between the first and second portions 540, 550 increases. As the second portion 550 moves away from the first portion 540 of the outer shell 530, the first portion 540, which is coupled to the thin elongated structure 520, pulls on the thin elongated structure 520 and thereby applies tension to the thin elongated structure 520. The tension applied to the thin elongated structure 520 by the first portion 540 of the outer shell 530 maintains the guidewire 510 in the rigid configuration.

To return the guidewire to the flexible configuration, the second portion 550 of the outer shell 530 may be rotated, relative to the thin elongated structure 520, in a second direction (arrow 557) (e.g., clockwise) opposite to the first direction (arrow 555). As the second portion of the outer shell is rotated (arrow 557) relative to the thin elongated structure 520, the engagement between the screw threads 524 and the threads 553 causes the second portion 550 of the outer shell 530 to move (arrow 558) toward the first portion 540 of the outer shell 530. As the second portion 550 of the outer shell 530 moves (arrow 558) toward the first portion 540 of the outer shell 530, the length of the gap G between the first and second portions 540, 550 decreases and the thin elongated structure 520 relaxes (e.g., the tension supplied to the thin elongated structure 520 by the first portion 540 of the outer shell 530 is reduced), which returns the guidewire 510 to the flexible configuration. Accordingly, the guidewire 510 according to one embodiment of the present disclosure may be moved between the flexible configuration and the rigid configuration by rotating (arrow 555, 556) the second portion 550 of the outer shell 530 to move the second portion 550 away from and toward, respectively, the first portion 540 of the outer shell 530 to increase and decrease, respectively, the length of the gap G between the first and second portions 540, 550 of the outer shell 530.

Additionally, in one or more embodiments, a tensioning mechanism 560 may be provided to aid in rotation (arrows 555, 557) of the second portion 550 of the outer shell 530 to move the guidewire 510 between the flexible and rigid configurations. In the illustrated embodiment, the tensioning mechanism 560 is provided on an outer surface 559 of the second portion 550 to increase the effective outer diameter of the second portion 550, which facilitates a user ergonomically grasping the tensioning mechanism 560 (e.g., between the user's thumb and forefinger) and rotating the tensioning mechanism 560 to rotate (arrows 555, 557) the second portion 550 of the outer shell 530 in the desired direction to achieve the desired tension or flexibility in the guidewire 510. In one or more embodiments, the tensioning mechanism 560 may be a thumbwheel that engages the outer surface 559 of the second portion 550. In one or more embodiments, the tensioning mechanism 560 may be any other suitable device configured to aid in rotation (arrows 555, 557) of the second portion 550 of the outer shell 530 (e.g., the tensioning mechanism 560 may be any other device fit over the outer surface 559 of the second portion 550 of the outer shell 530).

In one or more embodiments, the guidewire 510 may include one or more stops configured to maintain a minimum length of the gap G between the first portion 540 and the second portion 550 of the outer shell 530. The configuration of the one or more stops may the same as or similar to the configuration of the inner and outer stops 60, 80 illustrated in FIG. 1A. In one or more embodiments, the configuration of the one or more stops may be the same as or similar to the configuration of the inner stop 60 illustrated in FIG. 1B.

Figure 14A:
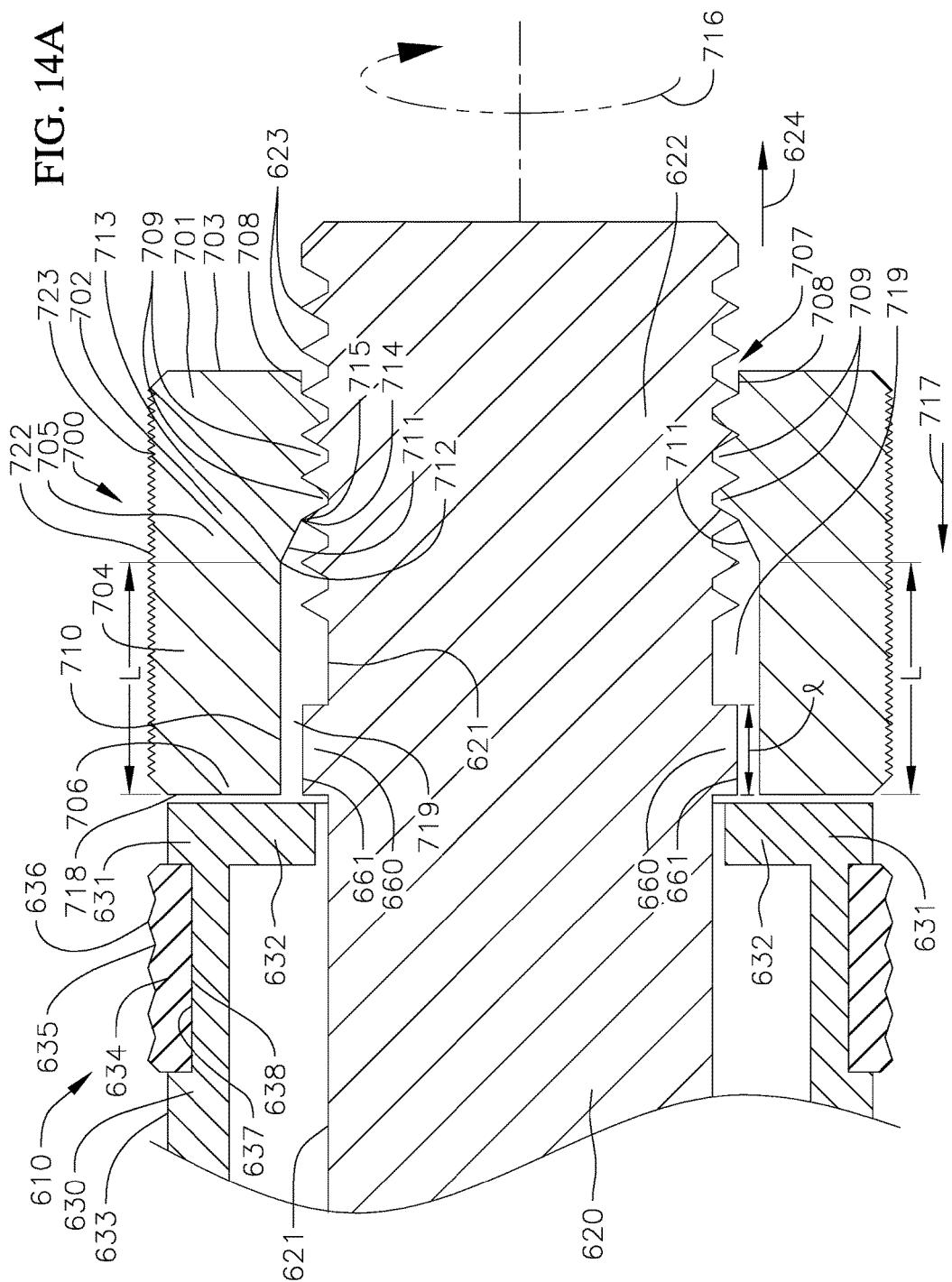
FIGS. 14A-14B are cross-sectional views of a guidewire and a tensioning mechanism according to a further embodiment of the present disclosure.
Figure 14B:
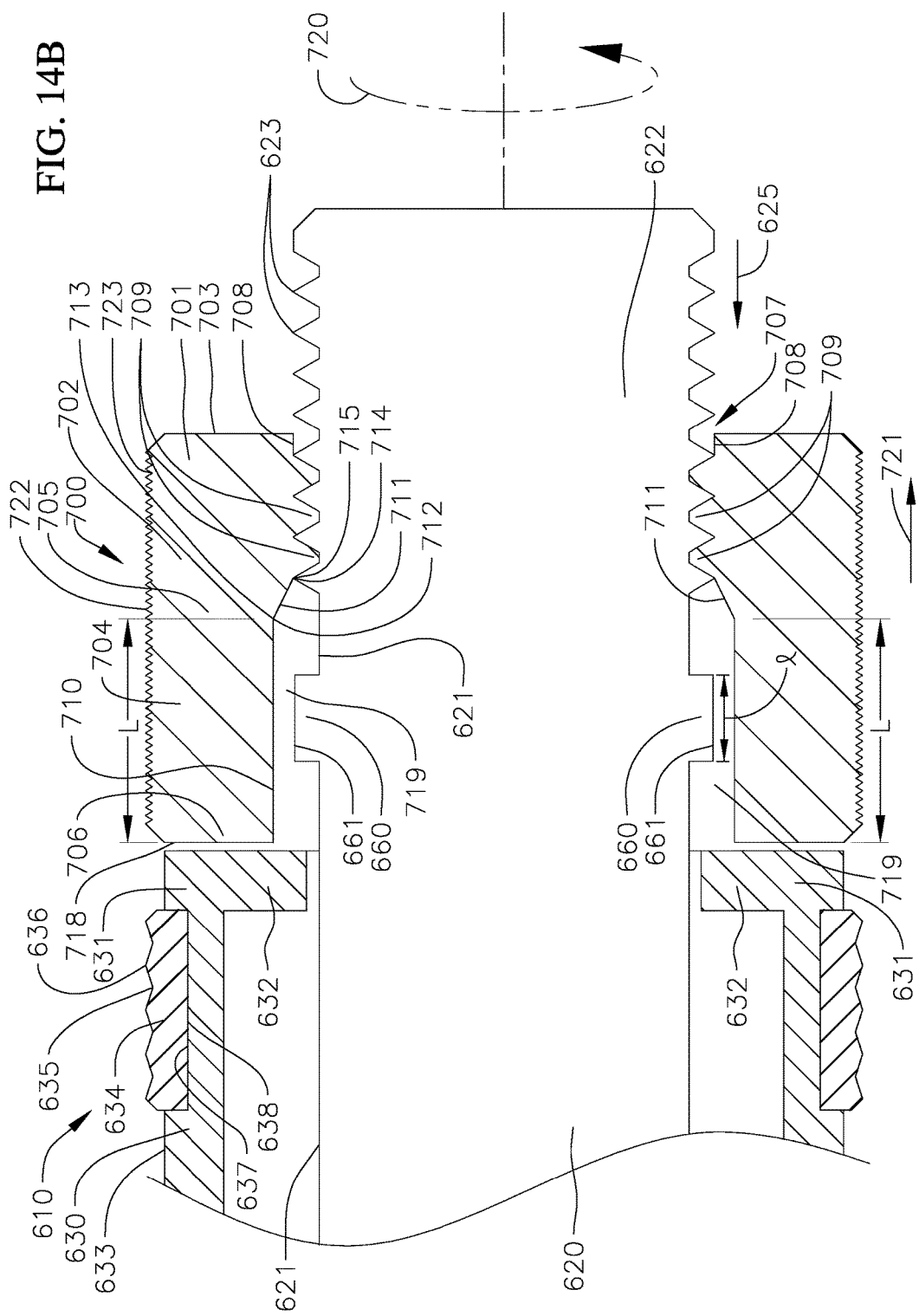

With reference now to FIGS. 14A-14B, a guidewire 610 according to another embodiment of the present disclosure includes a thin elongated structure 620 (e.g., a wire or a monofilament) and an outer shell 630 surrounding a portion of the thin elongated structure 620. In the illustrated embodiment, the outer shell 630 includes a single portion (e.g., the outer shell 630 is monolithic), although in one or more embodiments outer shell 630 may include two or more separate portions (e.g., two portions separated by a gap). The outer shell 630 may have any suitable configuration. For instance, in one or more embodiments, at least a portion of the outer shell 630 may have a spiral wound configuration (e.g., at least a portion of the outer shell 630 may be a coil spring). In one or more embodiments, at least a portion of the outer shell 630 may be solid. In one or more embodiments, the outer shell 630 may include both a solid portion and a spiral wound (e.g., coil spring) portion. In the illustrated embodiment, a portion (e.g., a tip portion) of the outer shell 630 is coupled (e.g., welded) to a portion (e.g., a tip portion) of the thin elongated structure 620.

In the illustrated embodiment, the guidewire 610 also includes an outer stop 660 extending outward (e.g., radially outward) from an outer surface 621 of the thin elongated structure 620. In one or more embodiments, the outer stop 660 may be integrally formed with the thin elongated structure 620 or the outer stop 660 may be formed separately from the elongated structure 620 and coupled to the thin elongated structure 620 by any suitable process, such as welding. In the illustrated embodiment, the outer stop 660 is an annular member (e.g., a ring) extending circumferentially around the thin elongated structure 620. In one or more embodiments, the outer stop 660 may not be an annular member (e.g., the outer stop 660 may include a series of protrusions arranged around the circumference of the thin elongated structure 620). Additionally, in the illustrated embodiment, the outer stop 660 is provided on a proximal end portion 622 of the thin elongated structure 620 that is exposed outside (e.g., not surrounded by) the outer shell 630.

In the illustrated embodiment, a proximal end 631 of the outer shell 630 includes an inwardly-extending flange 632 (e.g., an inwardly-turned flange 632 extending inward toward the thin elongated structure 620) configured to engage the outer stop 660 on the thin elongated structure 620. The engagement between the outer stop 660 and the inwardly-extending flange 632 is configured to prevent the outer shell 630 from completely covering the thin elongated structure 620, which might other occur, for example, due to the resiliency of the coil spring of the outer shell 630 (e.g., the engagement between the outer stop 660 and the inwardly-extending flange 632 is configured to maintain the proximal end portion 622 of the thin elongated structure 620 exposed outside of the outer shell 630).

Additionally, in the illustrated embodiment, an outer surface 661 of the outer stop 660 is recessed below an outer surface 633 of the outer shell 630. In one or more embodiments, recessing the outer surface 661 of the outer stop 660 below the outer surface 633 of the outer shell 630 is configured to enable a tensioning mechanism 700, described in detail below, to engage the proximal end 631 of the outer shell 630 to move the guidewire 610 between a flexible configuration, shown in FIG. 14A, and a rigid configuration, shown in FIG. 14B.

In the illustrated embodiment, the outer surface 621 of the thin elongated structure 620 includes screw threads 623. In one or more embodiments, the screw threads 623 may be provided only along the proximal end portion 622 (or a portion thereof) of the thin elongated structure 620. As described in more detail below, the screw threads 623 on the thin elongated structure 620 are configured to be threadedly engaged by the tensioning mechanism 700 to move the guidewire 610 between the flexible and rigid configurations.

With continued reference to the embodiment illustrated in FIGS. 14A-14B, the tensioning mechanism 700 includes a body portion 701 having a distal end 702 and a proximal end 703, and a flange portion 704 extending distally from the distal end 702 of the body portion 701. In one or more embodiments, the body portion 701 and the flange portion 704 are both annular members. Additionally, in the illustrated embodiment, the flange portion 704 includes a proximal end 705 connected to the distal end 702 of the body portion 701 and a free, distal end 706 opposite to the proximal end 705. In the illustrated embodiment, the body portion 701 of the tensioning mechanism 700 has a central opening 707 (e.g., a hole) and an inner surface 708 of the central opening 707 defines threads 709 configured to engage the screw threads 623 on the thin elongated structure 620. In the illustrated embodiment, the central opening 707 is a through hole extending completely through the body portion 701 (e.g., the central opening 707 extends from the distal end 702 to the proximal end 703 of the body portion 701).

In the illustrated embodiment, the size of an inner surface 710 of the flange portion 704 in transverse cross-section is larger than the size of the inner surface 708 of the central opening 707 in transverse cross-section (e.g., an inner diameter of the flange portion 704 is larger than an inner diameter of the central opening 707). Additionally, in the illustrated embodiment, the tensioning mechanism 700 includes a taper 711 (e.g., a draft or a chamfer) extending from the inner surface 710 of the flange portion 704 to the inner surface 708 of the central opening 707. The taper 711 tapers from a relatively wider end 712 at a proximal end 713 of the inner surface 710 of the flange portion 704 to a relatively narrower end 714 at a distal end 715 of the inner surface 708 of the central opening 707. The taper 711 is configured to aid in guiding the tensioning mechanism 700 onto the proximal end portion 622 of the thin elongated structure 620 (e.g., the taper 711 is configured to guide the proximal end portion 622 of thin elongated structure 620 into the central opening 707 in the body portion 701 as the tensioning mechanism 700 is attached to the proximal end portion 622 of the thin elongated structure 620). In one or more embodiments, the tensioning mechanism 700 may be provided without the taper 711 (e.g., the tensioning mechanism 711 may include a step between the inner surface 708 of the flange portion 704 and the inner surface 708 of the central opening 707).

The inner surface 710 of the flange portion 704 may have any suitable length L depending, for instance, on the distance the tensioning mechanism 700 is configured to pull the thin elongated structure 620 proximally relative to the outer shell 630 to move the guidewire 610 into the rigid configuration. In the illustrated embodiment, the length L of the inner surface 710 of the flange portion 704 is longer than the length l of the outer surface 661 of the outer stop 660 in a longitudinal direction of the thin elongated structure 620. In one or more embodiments, the tensioning mechanism 700 is configured to pull the thin elongated structure 620 proximally relative to the outer shell 630 up to a distance equal to the difference between the length L of the inner surface 710 of the flange portion 704 and the length l of the outer surface 661 of the outer stop 660. For instance, in one or more embodiments, the length L of the inner surface 710 of the flange portion 704 may be longer than length l of the outer surface 661 of the outer stop 660 by at least 0.5 cm or approximately 0.5 cm. In one or more embodiments, the length L of the inner surface 710 of the flange portion 704 may be longer than length l of the outer surface 661 of the outer stop 660 by at least 1 cm or approximately 1 cm (e.g., in a range from 1 cm or approximately 1 cm to 2 cm or approximately 2 cm).

In the illustrated embodiment, an outer surface 722 of the tensioning mechanism 700 includes one or more friction-inducing features 723, such as, for instance, projections (e.g., a knurled surface) and/or depressions (e.g., grooves, striations, and/or dimples) configured to aid a user in grasping the tensioning mechanism 700 and rotating the tensioning mechanism 700 to move the guidewire 610 between the rigid and flexible states, as described in more detail below. Additionally, in the illustrated embodiment, the outer surface 722 of the tensioning mechanism 700 is larger in transverse cross-section than the outer surface 633 of the outer shell 630 in transverse cross-section (e.g., the outer diameter of the tensioning mechanism 700 is larger than the outer diameter of the outer shell 630), which is configured to aid a user in ergonomically grasping the tensioning mechanism 700 and rotating the tensioning mechanism 700 to move the guidewire 610 between the rigid and flexible states. In one or more embodiments, the outer surface 722 of the tensioning mechanism 700 may have any other suitable size relative to the outer surface 633 of the outer shell 630 (e.g., the outer diameter of the tensioning mechanism 700 may be the same or substantially the same as the outer diameter of the outer shell 630).

In the illustrated embodiment, the guidewire 610 also includes a device 634 connected to the outer shell 630 to aid the user in grasping the guidewire 610 during rotation of the tensioning mechanism 700 to move the guidewire 610 between the rigid and flexible states, as described in more detail below. In one or more embodiments, an outer surface 635 of the device 634 includes one or more friction-inducing features 636, such as, for instance, projections (e.g., a knurled surface) and/or depressions (e.g., grooves, striations, and/or dimples). In the illustrated embodiment, the device 634 is provided on the outer shell 630 proximate to the proximal end 631 of the outer shell 630, although in one or more embodiments, the device 634 may be provided at any other suitable location along the length of the outer shell 630. In one or more embodiments, the device 634 may be an annular member (e.g., a donut-shaped device or a slotted ring) fit around the outer surface 633 of the outer shell 630. In one or more embodiments, at least the portion of the outer shell 630 along which the device 634 is provided is solid. Additionally, in one or more embodiments, the outer shell 630 may be configured to prevent the device 634 from rotating (e.g., slipping) relative to the outer shell 630. For instance, in one or more embodiments, the portion of the outer shell 630 along which the device 634 is provided may be non-circular (e.g., the portion of the outer shell 630 at which the device is provided may have a square transverse cross-section shape) and an inner surface of the device 634 engaging the outer shell 630 may have a mating (e.g., corresponding) configuration (e.g., a square transverse cross-sectional shape). In the illustrated embodiment, the portion of the outer shell 630 along which the device 634 is provided may include one or more flat surfaces 637 engaging one or more corresponding flat surfaces 638 on the device 634. The device 634 may be made out of any suitable material.

In operation, the tensioning mechanism 700 may first be connected to the guidewire 610. In the illustrated embodiment, the tensioning mechanism 700 may be connected to the guidewire 610 by inserting the proximal end portion 622 of the thin elongated structure 620 into the central opening 707 in the body portion 701 of the tensioning mechanism 700 and threading the threads 709 of the tensioning mechanism 700 onto the screw threads 623 of the thin elongated structure 620. In one or more embodiments, the taper 711 of the tensioning mechanism 700 aids in guiding the proximal end portion 622 of the thin elongated structure 620 into the central opening 707 of the tensioning mechanism 700.

Once is the tensioning mechanism 700 is connected to the guidewire 610, the tensioning mechanism 700 may be operated to move the guidewire 610 between the flexible and rigid configurations. In one embodiment, the guidewire 610 may be moved from the flexible configuration to the rigid configuration by rotating, relative to the thin elongated structure 620, the tensioning mechanism 700 in a first direction (arrow 716) (e.g., clockwise). In one embodiment, the tensioning mechanism 700 may be rotated by grasping the guidewire 610 (e.g., the device 634) with one hand (e.g., grasping the guidewire 610, such as the device 63, between the thumb and index finger of the user's left hand) and grasping the tensioning mechanism 700 with the user's other hand (e.g., grasping the tensioning mechanism 700 between the thumb and index finger of the user's right hand). As the tensioning mechanism 700 is rotated (arrow 716) relative to the thin elongated structure 620, the engagement between the threads 709 in the central opening 707 of the tensioning mechanism 700 and the screw threads 623 on the outer surface 621 of the thin elongated structure 620 moves (arrow 717) the tensioning mechanism 700 distally toward the proximal end 631 of the outer shell 630 (e.g., as the tensioning mechanism 700 is rotated (arrow 716), the engagement between the threads 709, 623 moves (arrow 717) the tensioning mechanism 700 distally along the thin elongated structure 620). Additionally, as the tensioning mechanism 700 is rotated (arrow 716) further, the flange portion 704 of the tensioning mechanism 700 passes over the outer stop 660 and an abutment surface 718 at the distal end 706 of the flange portion 704 engages (e.g., contacts) the proximal end 631 of the outer shell 630 (e.g., the inwardly-extending flange 632). In the illustrated embodiment, the inner surface of the 710 of the flange portion 704 of the tensioning mechanism 700 is larger in transverse cross-section than the outer surface 661 of the outer stop 660 in transverse cross-section (e.g., the inner diameter of the flange portion 704 of the tensioning mechanism 700 is larger than the outer diameter of the outer stop 660). Accordingly, in the illustrated embodiment, a recess 719 (e.g., a cavity) is defined between the inner surface 710 of the flange portion 704, the outer surface 621 of the thin elongated structure 620, and the outer surface 661 of the outer stop 660, which accommodates the outer stop 660 on the thin elongated structure 620 and allows the flange portion 704 to pass over the outer stop 660 and contact the proximal end 631 of the outer shell 630.

Continued rotation (arrow 716) of the tensioning mechanism 700 after the abutment surface 718 of the tensioning mechanism 700 engages the proximal end 631 of the outer shell 630 pulls (arrow 624) the thin elongated structure 620 proximally relative to the outer shell 630 such that a greater extent of the proximal end portion 622 of the thin elongated structure 620 extends through the central opening 707 in the tensioning mechanism 700. Pulling (arrow 624) the thin elongated structure 620 proximally applies tension to the thin elongated structure 620 because the thin elongated structure 620 is coupled to the outer shell 630 (e.g., at the distal tip). As the thin elongated structure 620 moves proximally (arrow 624) relative to the outer shell 630, the thin elongated structure 620, which is coupled to the outer shell 630 (e.g., at the distal tip), pulls proximally on the outer shell 630 and thereby compresses the outer shell 630. The compression applied to the outer shell 630 by the thin elongated structure 620 and the tension applied to the thin elongated structure 620 by the tensioning mechanism 700 maintains the guidewire 610 in the rigid configuration.

To return the guidewire to the flexible configuration, the tensioning mechanism 700 may be rotated, relative to the thin elongated structure 620, in a second direction (arrow 720) (e.g., counterclockwise) opposite to the first direction (arrow 716), as illustrated in FIG. 14B. As the tensioning mechanism 700 is rotated (arrow 720) relative to the thin elongated structure 620, the engagement between the screw threads 623 and the threads 709 causes the tensioning mechanism 700 to move (arrow 721) proximally away from the proximal end 631 of the outer shell 630. As the tensioning mechanism 700 moves (arrow 721) proximally relative to the outer shell 530, the thin elongated structure 620 moves distally (arrow 625) relative to the outer shell 630 such that a lesser extent of the proximal end portion 622 of the thin elongated structure 620 extends through the central opening 707 in the tensioning mechanism 700, which reduces the tension in the thin elongated structure 620 (e.g., relaxes the thin elongated structure 620) and thereby returns the guidewire 610 to the flexible configuration. Accordingly, the guidewire 610 according to one embodiment of the present disclosure may be moved between the flexible configuration and the rigid configuration by rotating (arrow 716, 720) the tensioning mechanism 700 to move the thin elongated structure 620 proximally and distally (arrows 624, 625) relative to the outer shell 630.

While certain embodiments of the present invention have been illustrated and described, it is understood by those of ordinary skill in the art that certain modifications and changes can be made to the described embodiments without departing from the spirit and scope of the present invention as defined by the following claims, and equivalents thereof. Although relative terms such as "outer," "inner," "upper," "lower," and similar terms have been used herein to describe a spatial relationship of one element to another, it is understood that these terms are intended to encompass different orientations of the various elements and components of the invention in addition to the orientation depicted in the figures. Additionally, as used herein, the term "substantially," "about," and similar terms are used as terms of approximation and not as terms of degree, and are intended to account for the inherent deviations in measured or calculated values that would be recognized by those of ordinary skill in the art. Moreover, the tasks described above may be performed in the order described or in any other suitable sequence. Additionally, the methods described above are not limited to the tasks described. Instead, for each embodiment, one or more of the tasks described above may be absent and/or additional tasks may be performed. Furthermore, as used herein, when a component is referred to as being "on" another component, it can be directly on the other component or components may also be present therebetween. Moreover, when a component is component is referred to as being "coupled" to another component, it can be directly attached to the other component or intervening components may be present therebetween.

Furthermore, although discussed with specific reference to guidewires, the invention may be applicable to other medical devices having a need for a distal portion with characteristic of lateral flexibility. For example, the present invention may be applicable for use in intravascular catheters (e.g., rapid exchange balloon catheters, stent delivery catheters, etc.) or intravascular rotational devices (atherectomy catheters, IVUS catheters, etc.).

What is claimed is:

1. A guidewire comprising:
a thin elongated structure; and
an outer shell around at least a portion of the thin elongated structure, the outer shell comprising a first portion and a second portion, the first portion and the second portion each being coupled to the thin elongated structure,
wherein the first portion is spaced from the second portion by a gap,
wherein the guidewire is configured to move between a flexible state and a rigid state,
wherein the gap has a non-zero first distance when the guidewire is in the flexible state, and
wherein the gap has a second distance greater than the first distance when the guidewire is in the rigid state.

2. The guidewire of claim 1, wherein the second distance is at least approximately 1 cm.

3. A guidewire comprising:
a thin elongated structure;
an outer shell around at least a portion of the thin elongated structure, the outer shell comprising a first portion and a second portion, the first portion and the second portion each being coupled to the thin elongated structure; and
an outer stop coupled to the thin elongated structure,
wherein the first portion is spaced from the second portion by a gap,
wherein the guidewire is configured to move between a flexible state and a rigid state,
wherein the gap has a first distance when the guidewire is in the flexible state,
wherein the gap has a second distance greater than the first distance when the guidewire is in the rigid state, and
wherein the outer stop is configured to maintain the first distance of the gap between the first portion and the second portion of the outer shell and prevent the first portion from contacting the second portion of the outer shell when the guidewire is in the flexible state.

4. The guidewire of claim 3, further comprising an inner stop coupled to the first portion of the outer shell, wherein the inner stop is configured to engage the outer stop when the guidewire is in the flexible state to maintain the first distance of the gap between the first portion and the second portion of the outer shell.

5. The guidewire of claim 3, wherein the outer stop extends into the gap between the first portion and the second portion of the outer shell, and wherein the outer stop is configured to engage a proximal end of the first portion of the outer shell when the guidewire is in the flexible state to maintain the first distance of the gap between the first portion and the second portion of the outer shell.

6. The guidewire of claim 1, wherein the outer shell comprises a spring.

7. The guidewire of claim 1, wherein the thin elongated structure comprises a wire or a cable.

8. The guidewire of claim 1, wherein a tip portion of the first portion of the outer shell is welded to a tip portion of the thin elongated structure.

9. The guidewire of claim 4, wherein the inner stop is between the outer stop and a distal end of the first portion of the outer shell.

10. The guidewire of claim 5, further comprising an inwardly extending flange at the proximal end of the first portion of the outer shell, and wherein the outer stop is configured to engage the inwardly extending flange when the guidewire is in the flexible state.

11. The guidewire of claim 10, wherein an outer surface of the outer stop is recessed below an outer surface of the first portion of the outer shell.

* * * * *